United States Patent
Ruff et al.

(10) Patent No.: US 11,667,954 B2
(45) Date of Patent: Jun. 6, 2023

(54) METHOD AND APPARATUS TO NORMALIZE QUANTITATIVE READOUTS IN SINGLE-CELL EXPERIMENTS

(71) Applicant: Mission Bio, Inc., South San Francisco, CA (US)

(72) Inventors: David Ruff, San Francisco, CA (US); Pedro Mendez, San Mateo, CA (US)

(73) Assignee: Mission Bio, Inc., South San Francisco, CA (US)

( * ) Notice: Subject to any disclaimer, the term of this patent is extended or adjusted under 35 U.S.C. 154(b) by 186 days.

(21) Appl. No.: 16/918,365

(22) Filed: Jul. 1, 2020

(65) Prior Publication Data

US 2021/0010061 A1    Jan. 14, 2021

Related U.S. Application Data

(60) Provisional application No. 62/869,237, filed on Jul. 1, 2019.

(51) Int. Cl.
| | | |
|---|---|---|
| C12Q 1/6806 | (2018.01) | |
| C12Q 1/6853 | (2018.01) | |
| C12Q 1/6804 | (2018.01) | |
| C12Q 1/6816 | (2018.01) | |

(52) U.S. Cl.
CPC ......... *C12Q 1/6806* (2013.01); *C12Q 1/6804* (2013.01); *C12Q 1/6816* (2013.01); *C12Q 1/6853* (2013.01); *C12Q 2525/185* (2013.01); *C12Q 2525/197* (2013.01); *C12Q 2565/514* (2013.01)

(58) Field of Classification Search
None
See application file for complete search history.

(56) References Cited

U.S. PATENT DOCUMENTS

| | | |
|---|---|---|
| 7,638,276 B2 | 12/2009 | Griffiths et al. |
| RE41,780 E | 9/2010 | Anderson et al. |
| 8,067,159 B2 | 11/2011 | Brown et al. |
| 8,257,925 B2 | 9/2012 | Brown et al. |
| 8,765,485 B2 | 7/2014 | Link et al. |
| 9,150,852 B2 | 10/2015 | Samuels et al. |
| 10,161,007 B2 | 12/2018 | Abate et al. |
| 2003/0156993 A1 | 8/2003 | Staats |
| 2004/0253613 A1 | 12/2004 | Taylor et al. |
| 2005/0019902 A1 | 1/2005 | Mathies et al. |
| 2005/0112639 A1 | 5/2005 | Wang et al. |
| 2007/0039866 A1 | 2/2007 | Schroeder et al. |
| 2007/0077572 A1 | 4/2007 | Tawfik et al. |
| 2007/0109530 A1 | 5/2007 | Ueno et al. |
| 2007/0141593 A1 | 6/2007 | Lee et al. |
| 2007/0206179 A1 | 9/2007 | Wang et al. |
| 2007/0231880 A1 | 10/2007 | Chang-Yen et al. |
| 2008/0014589 A1 | 1/2008 | Link et al. |
| 2008/0274458 A1 | 11/2008 | Latham et al. |
| 2009/0045064 A1 | 2/2009 | Simmons et al. |
| 2009/0098555 A1 | 4/2009 | Roth et al. |
| 2009/0122311 A1 | 5/2009 | Kanda |
| 2010/0015614 A1 | 1/2010 | Beer et al. |
| 2010/0028915 A1 | 2/2010 | Gualberto et al. |
| 2010/0055677 A1 | 3/2010 | Colston, Jr. et al. |
| 2010/0173394 A1 | 7/2010 | Colston, Jr. et al. |
| 2010/0285975 A1 | 11/2010 | Mathies et al. |
| 2011/0053798 A1 | 3/2011 | Hindson et al. |
| 2011/0056575 A1 | 3/2011 | Hong et al. |
| 2011/0059556 A1 | 3/2011 | Strey et al. |
| 2011/0103176 A1 | 5/2011 | Van Dam et al. |
| 2011/0104816 A1 | 5/2011 | Pollack et al. |
| 2011/0118151 A1 | 5/2011 | Eshoo et al. |
| 2011/0160078 A1 | 6/2011 | Fodor et al. |
| 2011/0217736 A1 | 9/2011 | Hindson |

(Continued)

FOREIGN PATENT DOCUMENTS

| | | |
|---|---|---|
| AU | 2013203624 A1 | 5/2013 |
| AU | 2013302867 A1 | 2/2015 |

(Continued)

OTHER PUBLICATIONS

Hayward RC, et al; (2006) "Dewetting instability during the formation of polymersomes from block-copolymer-stabilized double emulsions"; Langmuir 22(10); pp. 4457-4461.

(Continued)

*Primary Examiner* — Samuel C Woolwine
(74) *Attorney, Agent, or Firm* — Goodwin Procter LLP

(57) ABSTRACT

Provided herein are methods and systems for detection of nucleic acids for single cell samples. As part of the detection, a unique step of normalization of different single cell samples is included. One embodiment of the method includes i) selecting one or more target nucleic acid sequence of interest in an individual cell, where the target nucleic acid sequence is complementary to a nucleic acid in a cell; ii) providing a sample having a plurality of individual single cells and encapsulating one or more individual cell(s); iii) providing a sample normalization component to one or more encapsulated cell, where the normalization component comprises an exogenous nucleic acid having a known sequence; iv) providing nucleic acid primers for the target nucleic acid and the exogenous nucleic acid; v) providing a protease to each encapsulated cell and incubating the encapsulated cell with the protease in the drop to produce a cell lysate; vi) performing a nucleic acid amplification reaction to form an amplification product from the nucleic acid of a single cell, where the amplification product comprise amplicons of one or more target nucleic acid sequence and an amplicon for the exogenous nucleic acid; and vii) comparing the amplification products from the target amplicons and the exogenous nucleic acid amplicons and determining the copy number or sequence of the target nucleic acid in a single cell.

18 Claims, 10 Drawing Sheets

Specification includes a Sequence Listing.

(56) References Cited

U.S. PATENT DOCUMENTS

| | | |
|---|---|---|
| 2011/0311978 A1 | 12/2011 | Makarewicz, Jr. et al. |
| 2012/0010086 A1 | 1/2012 | Froehlich et al. |
| 2012/0045765 A1 | 2/2012 | Curran et al. |
| 2012/0094848 A1 | 4/2012 | Rigatti et al. |
| 2012/0122714 A1 | 5/2012 | Samuels et al. |
| 2012/0170739 A1 | 7/2012 | Karroumi et al. |
| 2012/0190032 A1 | 7/2012 | Ness et al. |
| 2012/0190033 A1 | 7/2012 | Ness et al. |
| 2012/0196288 A1 | 8/2012 | Beer et al. |
| 2012/0219947 A1 | 8/2012 | Yurkovetsky et al. |
| 2012/0220494 A1 | 8/2012 | Samuels et al. |
| 2012/0258870 A1 | 10/2012 | Schwartz et al. |
| 2012/0264646 A1 | 10/2012 | Link et al. |
| 2012/0270306 A1 | 10/2012 | Vacca et al. |
| 2012/0309002 A1 | 12/2012 | Link |
| 2012/0316074 A1 | 12/2012 | Saxonov |
| 2013/0032235 A1 | 2/2013 | Johnstone et al. |
| 2013/0046030 A1 | 2/2013 | Rotem et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0224736 A1 | 8/2013 | Marie et al. |
| 2013/0236901 A1 | 9/2013 | Potier et al. |
| 2013/0295567 A1 | 11/2013 | Link et al. |
| 2013/0295587 A1 | 11/2013 | Sjobom |
| 2014/0057799 A1 | 2/2014 | Johnson et al. |
| 2014/0154695 A1 | 6/2014 | Miller et al. |
| 2014/0155295 A1 | 6/2014 | Hindson et al. |
| 2014/0179544 A1 | 6/2014 | Steenblock et al. |
| 2014/0186840 A1 | 7/2014 | Ding et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378345 A1 | 12/2014 | Hindson et al. |
| 2014/0378349 A1 | 12/2014 | Hindson et al. |
| 2015/0232942 A1 | 8/2015 | Abate et al. |
| 2015/0298091 A1 | 10/2015 | Weitz et al. |
| 2015/0322507 A1 | 11/2015 | Zimmermann et al. |
| 2015/0361480 A1 | 12/2015 | Shannon et al. |
| 2015/0376609 A1 | 12/2015 | Hindson et al. |
| 2016/0061711 A1 | 3/2016 | Deka |
| 2016/0177375 A1 | 6/2016 | Abate et al. |
| 2016/0237486 A1 | 8/2016 | Zhou et al. |
| 2017/0002393 A1 | 1/2017 | Singh et al. |
| 2017/0005665 A1 | 1/2017 | Swaminathan et al. |
| 2017/0009274 A1 | 1/2017 | Abate et al. |
| 2017/0009275 A1 | 1/2017 | Menchen et al. |
| 2017/0022538 A1 | 1/2017 | Abate et al. |
| 2017/0121756 A1 | 5/2017 | Abate et al. |
| 2018/0056288 A1 | 3/2018 | Abate et al. |
| 2018/0216160 A1 | 8/2018 | Abate et al. |
| 2018/0237836 A1 | 8/2018 | Abate et al. |
| 2019/0010543 A1* | 1/2019 | Babiarz ................ C12Q 1/6869 |
| 2019/0112655 A1 | 4/2019 | Eastburn et al. |
| 2019/0169700 A1 | 6/2019 | Abate et al. |
| 2019/0218594 A1 | 7/2019 | Abate et al. |
| 2019/0241965 A1 | 8/2019 | Abate et al. |
| 2019/0330701 A1 | 10/2019 | Abate et al. |

FOREIGN PATENT DOCUMENTS

| | | |
|---|---|---|
| AU | 2016215298 A1 | 8/2017 |
| AU | 2019226236 A1 | 9/2019 |
| CA | 2881783 A1 | 2/2014 |
| CA | 3001986 A1 | 4/2016 |
| CA | 2974299 A1 | 8/2016 |
| CA | 2974306 A1 | 8/2016 |
| CN | 1693478 A | 11/2005 |
| CN | 104736725 A | 6/2015 |
| CN | 107107058 A | 8/2017 |
| CN | 107429426 A | 12/2017 |
| CN | 107530654 A | 1/2018 |
| CN | 108350488 A | 7/2018 |
| CN | 110088290 A | 8/2019 |
| DE | 10339452 A1 | 3/2005 |
| EP | 1547677 A1 | 6/2005 |
| EP | 2145955 A2 | 1/2010 |
| EP | 2565650 A1 | 3/2013 |
| EP | 2882872 A2 | 6/2015 |
| EP | 3160654 A2 | 5/2017 |
| EP | 3209419 A1 | 8/2017 |
| EP | 3253479 A2 | 12/2017 |
| EP | 3253910 A1 | 12/2017 |
| EP | 3337907 A1 | 6/2018 |
| EP | 3497228 A1 | 6/2019 |
| GB | 2519906 A | 5/2015 |
| GB | 2539836 B | 3/2017 |
| JP | 2013503630 A | 2/2013 |
| JP | 2015533079 A | 11/2015 |
| JP | 2018505671 A | 3/2018 |
| JP | 2018508198 A | 3/2018 |
| JP | 2018525004 A | 9/2018 |
| WO | 9412216 A1 | 6/1994 |
| WO | 2007140015 A2 | 12/2007 |
| WO | 2009050512 A2 | 4/2009 |
| WO | 2009054870 A2 | 4/2009 |
| WO | 2009111014 A2 | 9/2009 |
| WO | 2010148039 A2 | 12/2010 |
| WO | 2011047307 A1 | 4/2011 |
| WO | 2012011091 A2 | 1/2012 |
| WO | 2012048341 A1 | 4/2012 |
| WO | 2012083225 A2 | 6/2012 |
| WO | 2012109600 A2 | 8/2012 |
| WO | 2012142213 A2 | 10/2012 |
| WO | 2012156744 A3 | 11/2012 |
| WO | 2012162267 A2 | 11/2012 |
| WO | 2013119753 A1 | 8/2013 |
| WO | 2013126741 A1 | 8/2013 |
| WO | 2013130512 A2 | 9/2013 |
| WO | 2013134261 A1 | 9/2013 |
| WO | 2013173394 A2 | 11/2013 |
| WO | 2014028378 A2 | 2/2014 |
| WO | 2014028537 A1 | 2/2014 |
| WO | 2014047556 A1 | 3/2014 |
| WO | 2014083435 A2 | 6/2014 |
| WO | 2014093676 A1 | 6/2014 |
| WO | 2014108323 A1 | 7/2014 |
| WO | 2014138132 A2 | 9/2014 |
| WO | 2014151658 A1 | 9/2014 |
| WO | 2014153071 A1 | 9/2014 |
| WO | 2015031691 A1 | 3/2015 |
| WO | 2015069798 A1 | 5/2015 |
| WO | 2015120398 A1 | 8/2015 |
| WO | 2015157369 A1 | 10/2015 |
| WO | 2015189336 A1 | 12/2015 |
| WO | 2015200717 A2 | 12/2015 |
| WO | 2016064755 A1 | 4/2016 |
| WO | 2016065056 A1 | 4/2016 |
| WO | 2016126865 A1 | 8/2016 |
| WO | 2016126871 A2 | 8/2016 |
| WO | 2015164212 A9 | 10/2016 |
| WO | 2017031125 A1 | 2/2017 |
| WO | 2017218486 A1 | 12/2017 |
| WO | 2018119301 A1 | 6/2018 |
| WO | 2019067092 A1 | 4/2019 |
| WO | 2021003255 A1 | 1/2021 |

OTHER PUBLICATIONS

Herminghaus S, "Dynamical Instability of Thin Liquid Films Between Conducting Media"; Physical Review Letter, vol. 83, No. 12; Sep. 20, 1999; pp. 2359-2361.

Holland, et al; (1991) "Detection of specific polymerase chain reaction product by utilizing the 5'-3' exonuclease activity of Thermus aquaticus DNA polymerase"; PNAS, 88 (16); 7276-7280.

Holtyze C., et al; (2008) "Biocompatible surfactants for water-in-fluorocarbon emulsions"; Lab Chip 8; pp. 1632-1639.

(56) References Cited

OTHER PUBLICATIONS

Horton et al; "Gene splicing by overlap extension: tailor-made genes using the polymerase chain reaction"; Biotechniques, vol. 54; Mar. 1, 2013; pp. 129-133.
Hu, Hoa et al; (2009) "Mutation screening in 86 known X-linked mental retardation genes by droplet-based multiplex PCR and massive parallel sequencing"; HUGO J.3; pp. 41-49.
Huebner, et al; (2008) "Microdroplets: A sea of applications?"; Lab on a Chip, 8; pp. 1244-1254.
Hunkapiller and Hood, (1986) "Immunology: The Growing Immunoglobulin Gene Superfamily"; Nature, 323; pp. 15-16.
Hunt JA, et al; (1994) "Effect of pH on the stability and surface composition of emulsions made with whey protein isolate"; Journal of Agricultural and Food Chemistry.;42(10); pp. 2131-2135.
Huston et al; (1988) "Protein engineering of antibody binding sites: recovery of specific activity in an anti-digoxin single-chain Fv analogue produced in *Escherichia coli*"; Proc. Nal Acad Sci. U.S.A., 85; pp. 5879-5883.
International Preliminary Report on Patentability issued to PCT Application No. PCT/US2018/046762 dated Feb. 18, 2020.
International Preliminary Report on Patentability received for PCT Application Serial No. PCT/US2013/054517 dated Feb. 26, 2015, 14 pages.
International Preliminary Report on Patentability received for PCT Application Serial No. PCT/US2016/016438 dated Aug. 17, 2017, 10 pages.
International Preliminary Report on Patentability received for PCT Application Serial No. PCT/US2017/037175 dated Dec. 18, 2018, 3 pages.
International Search Report and Written Opinion for PCT/US20/14595, dated Apr. 29, 2020.
International Search Report and Written Opinion dated Jun. 4, 2020, to PCT Application No. PCT/US2020/014488.
International Search Report and Written Opinion received for International Application No. PCT/US2018/056575, dated Jan. 3, 2019, 15 pages.
International Search Report and Written Opinion received for International Application No. PCT/US2018/057410, dated Feb. 8, 2019, 14 pages.
International Search Report and Written Opinion received for PCT Application Serial No. PCT/US2013/054517 dated Feb. 21, 2014, 18 pages.
International Search Report and Written Opinion received for PCT Application Serial No. PCT/US2016/016438 dated Jun. 10, 2016, 14 pages.
International Search Report and Written Opinion to PCT Application No. PCT/US18/57410 dated Feb. 8, 2019.
International Search Report received for PCT Application Serial No. PCT/US2017/037175 dated Aug. 28, 2017, 3 pages.
Kawasaki, "Sample Preparation From Blood, Cells, and Other Fluids," Book, 1990, Chapter 18 pp. 146-152, PCR Protocols: A Guide to Methods and Applications.
Ki, JS., et al. (2005) "Integrated method for single-cell DNA extraction, PCR amplification, and sequencing of ribosomal DNA from harmful Dinoflagellates Cochlodium polykrikoides and Alexandrium catenella"; Marine Biotechnology, vol. 6; pp. 587-593.
Kiss MM, et al.(2008) "High-Throughput Quantitative Polymerase Chain Reaction in Picoliter Droplets"; Anal Chem 80 (23); pp. 8975-8981.
Kritikou Ekat; "It's cheaper in the Picolab"; Nat Rev Genet, 6; (Sep. 2005); pp. 668.
Kuster, et al., "Interfacing Droplet Microfluidics with Matrix-Assisted Laser Desorption/Ionization Mass Spectrometry: Label-Free Content Analysis of Single Droplets," Analytical Chemistry, 2013, pp. 1285-1289, 85, ACS Publications.
Lagally ET, et al; (2001) "Single-Molecule DNA Amplification and Analysis in an Integrated Microfluidic Device"; Analytical Chemistry.;73(3); pp. 565-570.

Lan, et al., "Single-Cell Genome Sequencing at Ultra-High-Throughput with Microfluidic Droplet Barcoding," journal, Jul. 2017, pp. 640-646, vol. 35, No. 7, Nature Biotechnology.
Lanza Vecchia et al; (1987) "The use of hybrid hybridomas to target human cytotoxic T lymphocytes"; Eur. J. Immunol. 17(1); pp. 105-111.
Leary JF. (1994) "Strategies for rare cell detection and isolation"; Methods Cell Biol.;42(Pt B); pp. 331-358.
Lim, Shuan and Abate Adam, (2013) "Ultrahigh-throughput sorting of microfluidic drops with flow cytometry"; Lab Chip13; pp. 4563-4572.
Link, et al; (2004) "Geometrically mediated breaknp of drops in microfluidic devices"; Phys Rev Lett. 92(5):054503.
Livak KJ and Schmittgen TD; (2001) "Analysis of Relative Gene Expression Data Using Real-Time Quantitative PCR and the $2^{-\Delta\Delta CT}$ Method"; methods.;25(4); pp. 402-408.
Longo MC, et al; (1990) "Use of uracil DNA glycosylase to control carry-over contamination in polymerase chain reactions"; Gene. ;93(1); pp. 125-128.
Malloggi F, et al; "Electrowetting-controlled droplet generation in a microfluidic flow-focusing device"; J. Phys.: Condens. Matter 19; (2007); 462101; 7 pages.
Marcus et al., "Parallel Picoliter RT-PCR Assays Using Microfluidics"; Analytical Chemistry, 78(3); (2006); pp. 956-958.
Markou Athina,et al; (2011) "Molecular Characterization of Circulating Tumor Cells in Breast Cancer by a Liquid Bead Array Hybridization Assay"; Clinical Chemistry 57:3; pp. 421-430.
Mary P Pascaline, et al; "Controlling droplet incubation using close-packed plug flow"; Biomicrojluidics 5; (2011); pp. 024101-1-024101-6.
Mazutis L, et al.; (2013) "Single-cell analysis and sorting using droplet-based microfluidics"; Nature protocols.8(5); pp. 870-891.
McDonald, et al; (2000) "Fabrication of microfluidic systems in poly( dimethylsiloxane"; Electrophoresis, 21 (I); pp. 27-40.
Medkov A, Martina et al; "Analyzing Cancer at Single Cell Resolution with Droplet Technology"; American Association of Cancer Research (AACR); Apr. 19, 2010; 1 page.
Metzker, Michael L. "Sequencing technologies—the next generation"; Nature Reviews Genetics, vol. 11 (Jan. 2010); pp. 31-46.
Miyazaki et al. (2013) "A new large-DNA-fragment delivery system based on integrase activity from an integrative and conjugative element"; Appl Environ Microbiol 79(14); pp. 4440-4447.
Miyazaki, K; (2002) "Random DNA fragmentation with endonuclease V: application to DNA shuffling"; Nucleic Acids Res. 30(24); e139.
Moon Sangjun, et al; "Drop-on-Demand Single Cell Isolation and Total RNA Analysis"; PloS ONE, vol. 6, Issue 3; e17455 (Mar. 2011); pp. 1-10.
Morton et al; (2008) "Crossing microfluidic streamlines to lyse, label and wash cellst"; Lab on a Chip, 8(9); pp. 1448-1453.
Mui B, et al; (1993) "Osmotic properties oflarge unilamellar vesicles prepared by extrusion"; Biophysical journal 64(2); pp. 443-453.
Nagrath Sunitha, et al; "Isolation of rare circulating tumour cells in cancer patients by microchip technology"; Nature 450(7173); Dec. 20, 2007; pp. 1235-1239.
Nakano M, et al. (2005) "Single-molecule reverse transcription polymerase chain reaction using water-in-oil emulsion"; J Biosci Bioeng 99; pp. 293-295.
Notification of Transmittal of the International Search Report and the Written Opinion of the International Searching Authority, or the Declaration, Int'l Application No. PCT/US2020/040470, dated Oct. 20, 2020, 27 pages.
Shlien et al., "Copy Number Variations and Cancer," Genome Med, Jun. 16, 2009, vol. 1, pp. 1-9.
International Preliminary Report on Patentability, Int'l Application No. PCT/US2020/040470, dated Dec. 28, 2021, 10 pages.
Ali, et al., "Rolling Circle Amplification: a Versatile Tool for Chemical Biology, Materials Science and Medicine," Journal, Mar. 18, 2017, pp. 3324-3341, vol. 43, Chem Soc Rev.
Baret, et al. "Fluorescence-activated Droplet Sorting (FADS): Efficient Microfluidic Cell Sorting Based on Enzymatic Activitys," Journal, 2009, pp. 1850-1858, 9(13), Lab on a Chip.

(56) References Cited

OTHER PUBLICATIONS

Bernath, et al., "In Vitro Compartmentalization by Double Emulsions: Sorting and Gene Enrichment by Fluorescence Activated Cell Sorting" Journal, 2004, pp. 151-157, Analytical Biochemistry 325.
Extended European Search Report received for European Patent Application Serial No. 15812857.9 dated Oct. 17, 2017, 7 pages.
Extended European Search Report received for European Patent Application No. 15853268.9 dated Sep. 3, 2018, 12 pages.
Extended European Search Report received for European Patent Application Serial No. 16747229.9 dated Sep. 10, 2018, 8 pages.
Extended European Search Report received for European Patent Application Serial No. 16837703.4 dated Nov. 29, 2018, 9 pages.
First Office action received for Chinese Patent Application Serial No. 2015800704110 dated Dec. 13, 2018, 2 pages.
Fu, Yusi et al (2015) "Uniform and accurate single-cell sequencing based on emulsion whole-genome amplification"; Proc Natl Acad Sci US A. 112(38); pp. 11923-11928.
Grover, et al. "Multiple Displacement Amplification as a pre-Polymerase Chain Reaction (pre-PCR) to Detect Ultra Low Population of Ralstonia Solanacearum (Smith 1896) Yabuchi et al. (1996)" Journal, 2009, pp. 539-543, 49(5), Lett Appl Microbiol.
International Preliminary Report on Patentability received for PCT Application Serial No. PCT/US2015/037822 dated Jan. 5, 2017, 7 pages.
International Preliminary Report on Patentability received for PCT Application Serial No. PCT/US2015/56743 dated May 4, 2017, 9 pages.
International Preliminary Report on Patentability received for PCT Application Serial No. PCT/US2016/016444 dated Aug. 17, 2017, 40 pages.
International Preliminary Report on Patentability received for PCT Application Serial No. PCT/US2016/47199 dated Mar. 1, 2018, 8 pages.
International Preliminary Report on Patentability received for PCT Application Serial No. PCT/US2017/046159 dated Feb. 21, 2019, 9 pages.
International Preliminary Report on Patentability received for PCT Application Serial No. PCT/US2017/068006 dated Jul. 4, 2019, 7 pages.
International Search Report and Written Opinion received for PCT Application Serial No. PCT/US2015/037822 dated Feb. 2, 2016, 9 pages.
International Search Report and Written Opinion received for PCT Application Serial No. PCT/US2015/56743 dated Mar. 3, 2016, 12 pages.
International Search Report and Written Opinion received for PCT Application Serial No. PCT/US2016/016444 dated Jul. 27, 2016, 43 pages.
International Search Report and Written Opinion received for PCT Application Serial No. PCT/US2016/47199 dated Dec. 12, 2016, 10 pages.
International Search Report and Written Opinion received for PCT Application Serial No. PCT/US2017/046159 dated Nov. 21, 2017, 12 pages.
International Search Report and Written Opinion received for PCT Application Serial No. PCT/US2017/068006 dated Mar. 26, 2018, 9 pages.
Nishikawa, Yohei et al (2015) "Monodisperse Picoliter Droplets for Low-Bias and Contamination-Free Reactions in Single-Cell Whole Genome Amplification" PLoS One 10(9); pp. e0138733.
Nunes, et al. "Dripping and Jelling in Microfluidic Multiphase Flows Applied to Particle and Fiber Synthesis," Journal, 2013, 46(11), J Phys D Appl Phys, pii 114002.
Rolando, et al. "Cell Host & Microbe," 2013, pp. 395-405, 13.4.
Sciambi et al. (2013) "Adding reagent to droplets with controlled rupture of encapsulated double emulsions"; Biomicrofluidics 7(4); pp. 1-6.
Sidore, et al (2016) "Enhanced sequencing coverage with digital droplet multiple displacement amplification"; Nuclei. Acids Res. 44(7):e66.; pp. 1-9.
Yu, et al (2014) "Mung bean nuclease treatment increases capture specificity of microdroplet-PCR based targeted DNA enrichment"; PLoS One 9(7):e103491; pp. 1-7.
Zhu, et al., "Highly Sensitive and Quantitative Detection of Rare Pathogens Through Agarose Droplet Microfluidic Emulsion PCR at the Single-Cell Level," Journal, 2012, pp. 3907-3913, 12(20), Lab on a Chip.
Abate, et al., "Efficient Encapsulation With Plug-Triggered Drop Formation," Journal, 2011, 84(3):031502, Physical Review E.
Abate, et al., "Faster Multiple Emulsification with Drop Splitting," Journal 2011, pp. 1911-1915, 11(11), Lab on a Chip.
Abate, et al., "High-Throughput Injection With Microfluidics Using Picoinjectors," Journal, Nov. 9, 2010, pp. 19163-19166, vol. 107 1 No. 45, PNAS.
Abate, et al., "Microfluidic Sorting With High-Speed Single-Layer Membrane Valves," Journal, 2010, pp. 203509-1-203509-3, Applied Physics Letters 96.
Abate, et al., "One-Step Formation of Multiple Emulsions in Microfluidics," Journal, 2011, pp. 253-258, 11(2), Lab on a Chip.
Abate, et al., "Photoreactive Coating for High-Contrast Spatial Patterning of Microfluidic Device Wettability," Journal, 2008, pp. 2157-2160, 8(12), Lab on a Chip.
Agresti, et al., "Correction for Ultrahigh-throughput Screening in Drop-Based Microfluidics for Directed Evolution," Journal, 2010, pp. 6550-6551, 107, Proc. Natl Acad Sci., US.
Agresti, et al., "Ultrahigh-Throughput Screening in Drop-Based Microfluidics for Firected Evolution," Journal, 2008, pp. 4004-4009, vol. 107, No. 9, PNAS.
Ahn, et al., "Electrocoalescence of Drops Synchronized by Size-Dependent Flow in Microfluidic Channels," Journal, 2006, pp. 264105-1-264105-3, Appl Phys Lett 88.
Allen, et al., "Single Virus Genomics: A New Tool for Virus Discovery," Journal, 2011, 6(3):e17722, PLoS One.
Arriaga, et al. "Ultrathin Shell Double Emulsion Templated Giant Unilamellar Lipid Vesicles With Controlled Microdomain Formations," Journal, 2014, pp. 950-956, 10(5), Small.
Atten, "Electrocoalescence of Water Droplets in an Insulating Liquid" Journal, 1993, pp. 259-569, J Electrostat 30.
AU Examination Report dated Oct. 3, 2018, to AU Patent Application No. 2013302867.
Barenholz, et al. "A Simple Method for the Preparation of Homogeneous Phospholipid Vesicles" Journal, 1977, pp. 2806-2810, 12(12), Biochemistry.
Battaglia, et al. "Polymeric Vesicle Permeability: A Facile Chemical Assay" Journal, 2006, pp. 4910-4913, 22(11), Langmuir.
Beer, et al. "On-Chip Single-Copy Real-0Time Reverse-Transcription PCR in Isolated Picoliter Droplets" Journal, 2008, pp. 1854-1858, Anal Chem 80.
Bird, et al. "Single-Chain Antigen-Binding Proteins" Journal, 1988, pp. 423-426, Science 242.
Blainey PC "The Future is Now: Single-Cell Genomics of Bacteria and Archaea" Journal, 2013, pp. 407-427, 37(3), FEMS Microbiology Reviews.
Brouzes, et al., "Droplet Microfluidic Technology for Single-Cell High-Throughput Screening," Journal, Aug. 25, 2009, pp. 14195-14200, vol. 106 No. 34, PNAS.
Brown, et al, "Current Techniques for Single-Cell Lysis" Journal, 2008, pp. S131-S138, J.R. Soc. Interface 5.
Caron, "Assessment of Bacterial Viabiligy Status by Flow Cytometry and Single Cell Sorting," Journal, 1998, pp. 988-998, 84(6), Journal of Applied Microbiology.
Chabert, et al. "Droplet Fusion by Alternating Current (AC) Field Electrocoalesence in Microchannels" Journal, 2005 pp. 3706-3715, Electrophoresis 26.
Chaffer, et al., "A Perspective on Cancer Cell Metastasis" Journal, Mar. 25, 2011, pp. 1559-1564, vol. 331, Science.
Chen, et al. "Influence of pH on the Stability of Oil-In-Water Emulsions Stabilized by a Splittable Surfactant," Journal, 2000, pp. 173-179, 170(2), Colloids and Surfaces A: Physicochemical and Engineering Aspects.
Chung, et al., "Droplet Dynamics Passing Through Obstructions in Confined Microchannel Flow," Journal, 2010, pp. 1151-1163, 9(6), Microfluidics Nanofluidics.

(56) References Cited

OTHER PUBLICATIONS

Clausell-Tormos, et al., "Droplet-Based Microfluidic Platforms for the Encapsulation and Screening of Mammalian Cells and Multicellular Organismsm" Journal, May 2008, pp. 427-437, Chemistry and Biology 15.
Dejournette CJ, et al; (2013) "Creating Biocompatible Oil-Water Interfaces without Synthesis: Direct Interactions between Primary Amines and Carboxylated Perfluorocarbon Surfactants"; Analytical chemistry.;85(21); pp. 10556-10564.
Dietrich et al; "Effects of UV irradiation and hydrogen peroxide on DNA fragmentation, motility and fertilizing ability of rainbow trout (*Oncorhynchus mykiss*) spermatozoa"; Theriogenology. vol. 64; (Nov. 2005) pp. 1809-1822.
Duffy DC, et al; (1998) "Rapid Prototyping ofMicrofluidic Systems in Poly(dimethylsiloxane)"; Anal. Chem. 70; pp. 4974-4984.
Eastburn Dennis J., et al; (2013) "Ultrahigh-Throughput Mammalian Single-Cell Reverse-Transcriptase Polymerase Chain Reaction in Microfluidic Drops"; Anal. Chem. 85; pp. 8016-8021.
Eastburn DJ,et al; (2013) "Picoinjection Enables Digital Detection of RNA with Droplet RT-PCR"; PloS one.;8(4): e62961.
Eastburn, et al., "Microfluidic Droplet Enrichment for Targeted Sequencing," journal, Apr. 14, 2015, pp. 1-8, vol. 43, Nucleic Acids Research.
Edd et al., (2008) Controlled encapsulation of single cells into monodisperse picoliter drop Lab on a Chip, 8(8); pp. 1262-1264.
EmPCR-amplification manual for GS-FLX series (May 2011); 454 Life Science Corp; 12 pages.
European search report and opinion dated Feb. 8, 2016 for EP Application No. 13829925.
Extended EP Search Report dated Feb. 8, 2016, to EP Patent Application No. 13829925.0.
Extended European Search Report received for European Patent Application Serial No. 16747224.0 dated May 24, 2018, 9 pages.
Final Office Action dated Apr. 18, 2018, to U.S. Appl. No. 15/047,555.
Final Office action dated Apr. 2, 2018, to U.S. Appl. No. 14/420,646.
Final Office Action dated Apr. 28, 2020, to U.S. Appl. No. 15/015,015.
Final Office Action dated Dec. 11, 2018, to U.S. Appl. No. 15/014,976.
Final office action dated Jan. 27, 2020, to U.S. Appl. No. 16/382,080.
Final Office Action dated Jun. 22, 2018, to U.S. Appl. No. 15/015,015.
Final Office action dated Sep. 21, 2018, to U.S. Appl. No. 15/317,393.
First Action Interview—Office Action dated Sep. 7, 2016, to U.S. Appl. No. 15/047,555.
First Office action received for Chinese Patent Application Serial No. 2013800532581 dated Feb. 22, 2016, 2 pages.
Frenz L, et al; (2009) "Reliable microfluidicon-chip incubation of droplets in delay-lines"; Lab on a Chip 9(10); pp. 1344-1348.
Garstecki P. et al; "Formation of droplets and bubbles in a microfluidic T-junction-scaling and mechanism of break-up"; Lab Chip 6; (2006); pp. 437-446.
Gevensleben H, et al; (2013) "Noninvasive Detection ofHER2 Amplification with Plasma DNA Digital PCR"; Clinical Cancer Research.; 19(12); pp. 3276-3284.
Gribskov, et al; (1986) "Sigma factors from *E. coli,* B. subtilis, phage SP01, and phage T4 are homologous proteins"; Nucl. Acids Res. 14(6):6745-6763.
Nikolova AN and Jones MN; (1996) "Effect of grafted PEG-2000 on the size and permeability of vesicles"; Biochimica et Biophysica Ada (BBA)—Lipids and Lipid Metabolism.; 1304(2); pp. 120-128.
Non-final office action dated Aug. 19, 2019, to U.S. Appl. No. 16/382,080.
Non-Final Office action dated Dec. 20, 2017, to U.S. Appl. No. 15/317,393.
Non-Final Office Action dated Jul. 12, 2017, to U.S. Appl. No. 115/015,015.
Non-Final Office action dated Jul. 14, 2017, to U.S. Appl. No. 14/420,646.
Non-final office action dated Mar. 6, 2020, to U.S. Appl. No. 16/658,991.
Non-Final Office Action dated Mar. 8, 2018, to U.S. Appl. No. 15/014,976.
Non-Final Office Action dated Nov. 13, 2017, to U.S. Appl. No. 15/015,015.
Non-Final Office Action dated Oct. 10, 2019, to U.S. Appl. No. 15/014,976.
Notice of Reasons for Rejection dated Dec. 19, 2019, to JP Patent Application No. 2017-539228.
Novak, et al; (2011) "Single-cell multiplex gene detection and sequencing with microfluidically generated agarose emulsions"; Angew Chem Int Ed Engl. 50(2):390-395.
Oberholzer,Thomas, et al; (1995) "Polymerase chain reaction in liposomes"; Chemistry & Biology vol. 2 No. 10; pp. 677-682.
O'Donovan B, et al; (2012) "Electrode-free picoinjection of microfluidic drops"; Lab Chip 12; pp. 4029-4032.
Okochi M et al; (2010) "Droplet-based gene expression analysis using a device with magnetic force-based-droplet-handling system"; J Biosci Bioeng. 109(2); pp. 193-197.
Pellegrino, et al., "High-Throughput Single-Cell DNA sequencing of AML Tumors with Droplet Microfluidics," bioRxiv preprint posted online, Oct. 13, 2017, 21 pages, http://dx.doi.org/10.1101/203158.
Perry DJ; (1999) "Solid-Phase Sequencing of Biotinylated PCR Products with Streptavidin-Coated Magnetic Beads"; Hemostasis and Thrombosis Protocols: Springer;. p. 49-54.
Piatek AS, et al; (1998) "Molecular beacon sequence analysis for detecting drug resistance in *Mycobacterium tuberculosis*";. Nat Biotechnol.16(4); pp. 359-363.
Priest Craig, et al; (2006) "Controlled electrocoalescence in microfluidics: Targeting a single lamella"; Appl Phys Lett, 89; pp. 134101-1-134101-3.
Sciambia Adam and Abate Adam R., (2015) "Accurate microfluidic sorting of droplets at 30 kHz"; Lab Chip 15(1); pp. 47-51.
Scotts. H, et al; (2011) "Microfluidic immunomagnetic multi-target sorting—a model for controlling deflection of paramagnetic beads"; Lab Chip 11; pp. 2577-2582.
Seemann R, et al; (2012) "Droplet based microfluidics"; Rep Prag Phys 75; pp. 016601.
Shui et al; (2011) "Microfluidic DNA fragmentation for on-chip genomic analysis" Nanotechnology 22(49): 494013. 7 pages.
Siegel Adam C,et al; (2007) "Microsolidics: Fabrication of Three-Dimensional Metallic Microstructures in Poly ( dimethylsiloxane )"; Adv Mater 19; pp. 727-733.
Song H, et al; (2006) "Reactions in droplets in microfluidic channels" Angew Chem Int Ed Engl 45; pp. 7336-7356.
Squires Tom M.; "Microfluidics: Fluid physics at the nanoliter scale"; Reviews of modern physics.;77(3); (Jul. 2005) pp. 977-1026.
Stone HA, et al; (2004) "Engineering flows in small devices: microfluidics toward a lab-on-a-chip"; Annu Rev Fluid Mech.;36; pp. 381-411.
Stott Shannon L; et al; "Isolation of circulating tumor cells using a microvortex-generating herringbone-chip"; PNAS vol. 107, No. 43; Oct. 26, 2010; pp. 18392-18397.
Sukovich, et al., "Bulk Double Emulsification for Flow Cytometric Analysis of Microfluidic Froplets," journal, Nov. 13, 2017, 5 pages, DOI:10.1039/c7an01695f, Royal Society of Chemistry.
Syed et al. (2009) "Next-generation sequencing library preparation: simultaneous fragmentation and tagging using in vitro transposition"; Nature Methods vol. 6; pp. 1-2.
Tadmor AD, et al; (2011) "Probing individual enviromnental bacteria for viruses by using microfluidic digital PCR" Science.;333(6038); pp. 58-62.
Takagi et al. (2005) "Continuous particle separation in a microchannel having asymmetrically arranged multiple branches" Lab Chip, 5(7); pp. 778-784.
Tamminen, et al. "Single Gene-Based Distinction of Individual Microbial Genomes from a Mixed Population of Microbial Cells," Journal, 2015, pp. 1-10, 6:195, Front Microbiol.
Teh SY,et al; "Droplet microfluidics"; Lab Chip 8; (2008); pp. 198-220.
Tewhey Ryan, et al; "Microdroplet-based PCR enrichment for large-scale targeted sequencing"; Nature Biotechnology, vol. 27 No. II; (Nov. 2009); pp. 1025-1035.

(56) References Cited

OTHER PUBLICATIONS

Thomann Y, et al; (2005) "PMMA Gradient Materials and in situ Nanocoating via Self-Assembly of Semifluorinated Hyperbranched Amphiphiles"; Macromolecular Chemistry and Physics.;206(1); pp. 135-141.

Thorsen T, et al; (2001) "Dynamic pattern formation in a vesicle-generating microfluidic device"; Phys Rev Lett 86; pp. 4163-4166.

Tsai Scott S. H., et al; (2011) "Microfluidic immunomagnetic multi-target sorting—a model for controlling deflection of paramagnetic beads"; Lab Chip 11; pp. 2577-2582.

Ullal, et al; (2014) "Cancer cell profiling by barcoding allows multiplexed protein analysis in fine needle aspirates"; Sci Transl Med. 6(219):219ra9; pp. 1-22.

Utada, et al; (2007) "Dripping to jetting transitions in co flowing liquid streams"; Phys Rev Lett. Aug. 31, 2007;99(9; pp. 094502-1-094502-4.

Vanapalli SA,et al; "Hydrodynamic resistance of single confined moving drops in rectangular microchannels"; Lab Chip 9 (2009); pp. 982-990.

Vickers, et al., (2006) "Generation of Hydrophilic Poly(dimethylsiloxane) for High-Performance Microchip Electrophoresis"; Anal. Chem, 78(21); pp. 7446-7452.

Wang C, et al; (2012) "Amphiphilic building blocks for self-assembly: from amphiphiles to supra-amphiphiles"; Accounts of Chemical Research 45(4); pp. 608-618.

Wheeler et al, (2005) "Digital microfluidics with in-line sample purification for proteomics analyses with MALDI-MS"; Anal Chem. 77(2); 534-540.

Whitcombe D, et al; (1999) "Detection of PCR products using self-probing amplicons and fluorescence"; Nature biotechnology 17(8); pp. 804-807.

Whitesides GM. (2006) The origins and the future of microfluidics. Nature 442(7101); pp. 368-373.

Written Opinion received for PCT Application Serial No. PCT/US2017/037175 dated Aug. 28, 2017, 4 pages.

Xia YN, et al; (1998) "Soft lithography"; Angew Chem Int Edit 37; pp. 551-575.

Zeng, et al., "High Performance Single Cell Genetic Analysis Using Microfludic Emulsion Generator Arrays," journal, Apr. 15, 2010, pp. 3138-3190, vol. 82, No. 8, Analytical Chemistry.

Zheng, B, et al; (2004) "Formation of droplets of in microfluidic channels alternating composition and applications to indexing of concentrations in droplet-based assays"; Anal Chem 76; pp. 4977-4982.

Zhong Qun, et al; (2011) "Multiplex digital PCR: breaking the one target per color barrier of quantitative PCR"; Lab Chip 11; pp. 2167-2174.

Zhu et al., (2001) "Reverse transcriptase template switching: a SMART approach for full-length cDNA library construction"; BioTechniques 30: pp. 892-897.

Zien TF; (1969) "Hydrodynamics of bolus flow—an analytical approach to blood flow in capillaries"; Math Biophys, 31; pp. 681-694.

Final Office Action dated Oct. 18, 2019, to U.S. Appl. No. 16/164,595.

Non-Final Office Action dated Apr. 18, 2019, to U.S. Appl. No. 16/164,595.

* cited by examiner

FIG. 1

[NIH] U.S. National Library of Medicine > NCBI National Center for Biotechnology Information    Sign in to NCBI BLAST® » blastn suite » RID-CERX3Y1Y015    Home  Recent Results  Saved Strategies  Help

BLAST Results

Edit and Resubmit  Save Search Strategies  ▷Formatting options  ▷Download
Job title: Nucleotide Sequence  You[Tube]  How to read this page  Blast report description  [NEW] Click here to see the new BLAST results page RID              CERX3Y1Y015 (Expires on 05-01 04:33 am)
Query ID         lcl|Query_198855                    Database Name  nr
Description      None                                Description    Nucleotide collection (nt)
Molecule type    dna                                 Program        BLASTN 2.9.0 + ▷Citation
Query Length     362

ⓘ No significant similarity found. For reasons why click here

Other reports: ▷Search Summary

FIG. 2

[NIH] U.S. National Library of Medicine > NCBI National Center for Biotechnology Information    Sign in to NCBI BLAST® » blastn suite » RID-CERYZ3Z6014    Home  Recent Results  Saved Strategies  Help

BLAST Results

Edit and Resubmit  Save Search Strategies  ▷Formatting options  ▷Download
Job title: Nucleotide Sequence  You[Tube]  How to read this page  Blast report description  [NEW] Click here to see the new BLAST results page RID         CERYZ3Z6014 (Expires on 05-01 04:34 am)
Query ID    lcl|Query_3647                    Database Name  refseq_rna
Description None                              Description    NCBI Transcript Reference Sequences
Molecule type dna                             Program        BLASTN 2.9.0 + ▷Citation
Query Length 362

ⓘ No significant similarity found. For reasons why click here

Other reports: ▷Search Summary

FIG. 3

NIH > U.S. National Library of Medicine > NCBI National Center for Biotechnology Information          Sign in to NCBI BLAST® » blastn suite » RID-CESGUK3V015                                    Home  Recent Results  Saved Strategies  Help

BLAST Results

Edit and Resubmit  Save Search Strategies  ▷Formatting options  ▷Download

Job title: Nucleotide Sequence  You[Tube]  How to read this page  Blast report description  [NEW] Click here to see the new BLAST results page RID          CESGUK3V015 (Expires on 05-01 04:44 am)
Query ID     lcl|Query_190747                    Database Name  genomic/9606/RefSeqGene
Description  None                                Description    Align your sequences to the RefSeqGene set
Molecule type dna                                Program        BLASTN 2.9.0 + ▷Citation
Query Length 362

ⓘ No significant similarity found. For reasons why click here

Other reports: ▷Search Summary

FIG. 4

NIH U.S. National Library of Medicine > NCBI National Center for Biotechnology Information Sign in to NCBI BLAST® » blastn suite » RID-CET2024D014

Home  Recent Results  Saved Strategies  Help

BLAST Results

Edit and Resubmit  Save Search Strategies  ▷Formatting options  ▷Download
Job title: Nucleotide Sequence  You[Tube] How to read this page  Blast report description  [NEW] Click here to see the new BLAST results page

| | |
|---|---|
| RID | CET2024D014 (Expires on 05-01 04:53 am) |
| Query ID | lcl|Query_155549 |
| Description | None |
| Molecule type | dna |
| Query Length | 362 |

Database Name  pat
Description    Nucleotide sequences derived from the Patent division of GenBank
Program        BLASTN 2.9.0 + ▷Citation ⓘ No significant similarity found. For reasons why click here Other reports: ▷Search Summary

> NIH U.S. National Library of Medicine > NCBI National Center for Biotechnology Information        Sign in to NCBI Primer-BLAST » JOB ID:Q0mcogSACSguFgwTAXMoIXtoORNWeyIOVw

Primer-BLAST Results

Input PCR template    none

Specificity of primers    No target templates were found in selected database: Genome database (reference assembly only) for selected species
(Organism limited to Homo sapiens)

Other reports    ▷ Search Summary

⊟ Detailed primer reports

| Primer pair 1 | | | | | | | |
|---|---|---|---|---|---|---|---|
| | Sequence (5'->3') | Length | Tm | GC% | Self complementarity | Self 3' complementarity | |
| Forward primer | AATTCTTCTCTCTGCGCTG | 21 | 58.11 | 47.62 | 4.00 | 4.00 | |
| Reverse primer | TCCTAAGAGTAGCATCAGCTAGC | 23 | 58.93 | 47.83 | 6.00 | 6.00 | |

FIG. 7

NIH › U.S. National Library of Medicine › NCBI National Center for Biotechnology Information          Sign in to NCBI Primer-BLAST » JOB ID:qqB1KnEDfKtblWaQa_BCohHrU5A8-EINPQ

Primer-BLAST Results

Input PCR template    none
Specificity of primers   No target templates were found in selected database: Refseq mRNA (Organism limited to Homo spaiens)
Other reports    ▷ Search Summary ⊟ Detailed primer reports

Primer pair 1

|  | Sequence (5'->3') | Length | Tm | GC% | Self complementarity | Self 3' complementarity |
|---|---|---|---|---|---|---|
| Forward primer | AATTCTTCTCTCTCTGCGCTG | 21 | 58.11 | 47.62 | 4.00 | 4.00 |
| Reverse primer | TCCTAAGAGTAGCGATCAGCTAGC | 23 | 58.93 | 47.83 | 6.00 | 6.00 |

FIG. 8

Primer-BLAST Results

Input PCR template: none
Specificity of primers: Target templates were found in selected database. Genome database (reference assembly only) for selected species (Organism limited to Mus musculus)
Other reports: ▸ Search Summary

Detailed primer reports

Primer pair 1

| | Sequence (5'->3') | Length | Tm | GC% | Self complementarity | Self 3' complementarity |
|---|---|---|---|---|---|---|
| Forward primer | AATTCTTCTCTCTGCGCTG | 21 | 58.11 | 47.62 | 4.00 | 4.00 |
| Reverse primer | TCCTAAGAGTACGGATCAGCTAGC | 23 | 58.93 | 47.83 | 6.00 | 6.00 |

Products on target templates

>NC_000069.6 Mus musculus strain C57BL/6J chromosome 3, GRCm38.p4 C57BL/6J product length = 2038
Forward primer   1         AATTCTTCTCTCTGCGCTG           21
Template         63428221  TT.CT..........T.....         63428241

Forward primer   1         AATTCTTCTCTCTGCGCTG           21
Template         63430258  T.GAA..........T.....         63430238

FIG. 9

NIH > U.S. National Library of Medicine > NCBI National Center for Biotechnology Information          Sign in to NCBI Primer-BLAST » JOB ID:j4VQD9uM1lTxGswfwX_oLbtk-R-Wd-ICIw

Primer-BLAST Results

Input PCR template    none
Specificity of primers   No target templates were found in selected database: Refseq mRNA (Organism limited to Homo spaiens)
Other reports         ▷ Search Summary

☐ Detailed primer reports

| Primer pair 1 | Sequence (5'→3') | Length | Tm | GC% | Self complementarity | Self 3' complementarity |
|---|---|---|---|---|---|---|
| Forward primer | AATTCTTCTCTCTCTGCGCTG | 21 | 58.11 | 47.62 | 4.00 | 4.00 |
| Reverse primer | TCCTAAGAGTAGCGATCAGCTAGC | 23 | 58.93 | 47.83 | 6.00 | 6.00 |

FIG. 10

METHOD AND APPARATUS TO NORMALIZE QUANTITATIVE READOUTS IN SINGLE-CELL EXPERIMENTS

RELATED APPLICATIONS

This application takes priority to U.S. Provisional Application Ser. No. 62/869,237 filed Jul. 1, 2019 by Mendez P., et al., and entitled 'Method and Apparatus to Normalize Quantitative Readouts in Single-Cell Experiments'; incorporated by reference herein.

FIELD

This invention relates generally to methods and systems for the targeted detection of DNA, RNA, and Protein, to the identification of cell subtypes based upon the DNA, RNA, or protein, and more particularly to methods of normalizing samples while performing these detection and characterization analysis from single cells.

SEQUENCE LISTING

The instant application contains a Sequence Listing which has been submitted electronically in ASCII format and is hereby incorporated by reference in its entirety. Said ASCII copy, created on Sep. 23, 2020, is named MSB-014US SL.txt and is 1,753 bytes in size.

BACKGROUND

Extensive research has been conducted in examining the role of tumor suppressor genes and proto-oncogenes in cancer development. One theory of cancer development postulates that the loss of tumor suppressor gene activity through deletion or inactivation of both alleles of a particular tumor suppressor gene (e.g. p53). See Wang L, -H, Wu C, -F, Rajasekaran N, Shin Y, K: Loss of Tumor Suppressor Gene Function in Human Cancer: An Overview. Cell Physiol Biochem 2018; 51:2647-2693. doi: 10.1159/00049, incorporated by reference herein.

An important aspect of nucleic acid analysis gene copy number and mutations mutation is often neglected, and that is designing approaches to standardize and normalize between different samples. Typically, biological samples used to prepare nucleic acid libraries for downstream analyses are homogeneously processed according to standardized assay protocols without regard to customized procedures for each sample. A particularly important measurement, in particular across different samples, is nucleic acid concentration of nucleic acid libraries. This is in part because performance of many modern nucleic acid analysis technologies is dependent on the nucleic acid concentration of input nucleic acids.

Effective normalization approaches for the analysis of the nucleic acids (e.g. gDNA) of single cell samples for the analysis of tumor suppressor and oncogene copy number alterations and variations for robust assay systems has yet to be developed. Likewise, such approaches have not been developed for proteins and other cell analytes at the single cell level. There is an unmet need for the application of these approached to single cell analysis. The inventions provided herein address this need.

BRIEF SUMMARY

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

Microfluidic, droplet-based technology described herein allows the quantitative interrogation of hundreds of analytes, in thousands of independent single cells in a single experiment, using amplification techniques such as PCR-based assays. Each drop acts as an independent microreactor. Embodiments of the invention allow single cell analysis from different cells to be normalized.

Data normalization of multiplexed PCR-based assays using both endogenous controls and external reference samples, allows robust correction of differences in PCR efficiency, across independent samples and experiments. These methods provided herein are useful not only to understand sources of variability of laboratory developed tests (LDTs), but also to monitor assay performance metrics.

High-throughput single-cell experiments, by nature are quantitative, and intra- and/or inter-experimental normalization strategies are in high demand. Additionally, the methods provided herein allow the normalization of single cell sample comparative analysis of not only nucleic acids but other cellular analytes such as proteins.

In a first aspect, embodiments of the invention are directed to methods for detection of nucleic acid detection for single cell samples. As part of the detection, a unique step of normalization of different single cell samples is included. An exemplary embodiment of the method includes, independent of order, the following steps: selecting one or more target nucleic acid sequence of interest in an individual cell, where the target nucleic acid sequence is complementary to a nucleic acid in a cell; providing a sample having a plurality of individual single cells and encapsulating one or more individual cell(s); providing a sample normalization component to one or more encapsulated cell, where the normalization component comprises an exogenous nucleic acid having a known sequence; providing nucleic acid primers for the target nucleic acid and the exogenous nucleic acid; providing a protease to each encapsulated cell and incubating the encapsulated cell with the protease in the drop to produce a cell lysate; performing a nucleic acid amplification reaction to form an amplification product from the nucleic acid of a single cell, where the amplification product comprise amplicons of one or more target nucleic acid sequence and an amplicon for the exogenous nucleic acid; and comparing the amplification products from the target amplicons and the exogenous nucleic acid amplicons and determining the copy number or sequence of the target nucleic acid in a single cell.

In some implementations of the above embodiment, the sample normalization reagent in step iii) is a synthetic nucleic acid having a known sequence. In some embodiments, the sample normalization reagent in step iii) is an aliquot or portion of a cell extract comprising the exogenous nucleic acid. In sonic implementations of the above embodiment, the sample normalization reagent in step iii) is a whole cell extract. In some embodiments, the cell extract comprising the exogenous nucleic acid is selected from a non-human cell line (e.g., vertebrate non-mammalian, mammalian, insect, reptilian, plant, etc.). In some embodiments, the synthetic nucleotide comprises a nucleotide sequence having at least 100 consecutive nucleotides of SEQ ID NO: 1. In some embodiments, the synthetic nucleotide comprises SEQ ID NO:1.

In some implementations of the first embodiment, in step iv), the amounts of the amplification products from the target amplicons and the exogenous nucleic acid amplicons are determined and compared.

In some implementations of the first embodiment, a reverse transcription reaction is performed to produce a reverse transcription product. In some implementations, the reverse transcription step is performed to produce a reverse transcription product before a nucleic acid amplification step. In sonic implementations, the reverse transcription and amplification reactions are performed in a single step.

In some embodiments, the reaction mixture further comprises amplification primers complementary to the synthetic nucleic acid. In some embodiments, the amplification primers have nucleic acid sequences comprising SEQ ID NO:2 and SEQ ID NO:3. In some embodiments, the reaction mixture includes a reverse transcriptase and comprises performing reverse transcription on the RNA to produce a reverse transcription product and amplifying the reverse transcription product, wherein performing reverse transcription and amplifying occur in a single step.

In some embodiments, the method further includes performing a nucleic acid sequencing reaction of an amplification product.

In some embodiments, the method further includes performing an analysis of the copy number variation of one or more selected target nucleic acid sequence.

In some embodiments, the method further includes the identification or determining the presence of signature mutations at a single-cell level.

In some embodiments, the affinity reagent may include a bead, solid support, or the like.

In some embodiments, at least one primer of a nucleic acid amplification primer set comprises a barcode identification sequence and the method further includes first providing an affinity reagent that has a nucleic acid sequence complementary to the identification barcode sequence of one of more nucleic acid primer of a primer set, where the affinity reagent having the nucleic acid sequence complementary to the identification barcode sequence is capable of binding to a nucleic acid amplification primer set having a barcode identification sequence; and second contacting an affinity reagent to the amplification product having amplicons of one or more target nucleic acid sequence under conditions sufficient for binding of the affinity reagent to the target nucleic acid to form an affinity reagent bound target nucleic acid.

In another aspect, methods of identifying and characterizing clonal sub populations of cells are provided. An exemplary embodiment is a method having the following steps: selecting one or more target nucleic acid sequence of interest in an individual cell, where the target nucleic acid sequence is complementary to a nucleic acid in a cell; providing a sample having a plurality of individual single cells and encapsulating one or more individual cell(s); providing a sample normalization component to one or more encapsulated cell, where the normalization component comprises an exogenous nucleic acid having a known sequence; providing nucleic acid primers for the target nucleic acid and the exogenous nucleic acid; providing a protease to each encapsulated cell and incubating the encapsulated cell with the protease in the drop to produce a cell lysate; performing a nucleic acid amplification reaction to form an amplification product from the nucleic acid of a single cell, said amplification product comprising amplicons of one or more target nucleic acid sequence and an amplicon for the exogenous nucleic acid; comparing the amplification products from the target amplicons and the exogenous nucleic acid amplicons; and determining the copy number or sequence of the target nucleic acid in a single cell and using the copy number of one or more target nucleic acid to characterize a single cell.

In another aspect, methods of identifying and characterizing clonal sub populations of cells are provided. An exemplary embodiment has the steps of: conjugating barcode sequences flanked by PCR priming sites onto antibodies, where a barcode sequence is specific to an antibody; performing a cell staining step using the barcode-conjugated antibodies; partitioning or separating individual cells or portion thereof and encapsulating one or more individual cell(s) or portion thereof in a reaction mixture comprising a protease and optionally a reverse transcriptase; providing a sample normalization component to one or more encapsulated cell, where the normalization component comprises an exogenous nucleic acid or polypeptide having a known sequence; incubating the encapsulated cell with the protease; providing one or more nucleic acid amplification primer sets, wherein one or more primer of a primer set comprises a barcode identification sequence associated with an antibody; performing a nucleic acid amplification reaction to produce one or more amplicons; providing an affinity reagent that comprises a nucleic acid sequence complementary to the identification barcode sequence of one of more nucleic acid primer of a primer set, where the affinity reagent having a nucleic acid sequence complementary to the identification barcode sequence is capable of binding to a nucleic acid amplification primer set having a barcode identification sequence; contacting an affinity reagent to the amplification product comprising amplicons of one or more target nucleic acid sequence under conditions sufficient for binding of the affinity reagent to the target nucleic acid to form an affinity reagent bound target nucleic acid; characterizing one or more protein by sequencing a barcode of an amplicon; and further characterizing the protein or nucleic acid that encodes the protein.

In another aspect, amplification primer sets for the normalization of an amplification reaction are provided. An exemplary amplification primer set includes SEQ ID NO:2 and SEQ ID NO:3.

In another aspect, embodiments are provided for performing an analysis of the copy number variation of one or more selected target nucleic acid sequence.

In another aspect, embodiments are provided for performing an analysis of the copy number variation of one or more selected target nucleic acid sequence is performed and used to characterize one or more single cell.

In another aspect, embodiments are provided for performing an analysis of the copy number variation of one or more selected target nucleic acid sequence is performed and used to characterize one or more single cell to determine if the cell is mutated, pre-cancerous, or a cancer cell.

In another aspect, embodiments are provided for performing an analysis of a cancer cell pre-cancer cell subtype is performed.

In another aspect, embodiments are provided for performing an analysis includes a determination of structure variations, single nucleotide variations, or copy number variations or one or more target nucleic acid sequence.

BRIEF DESCRIPTION OF THE DRAWINGS

Figure 1:
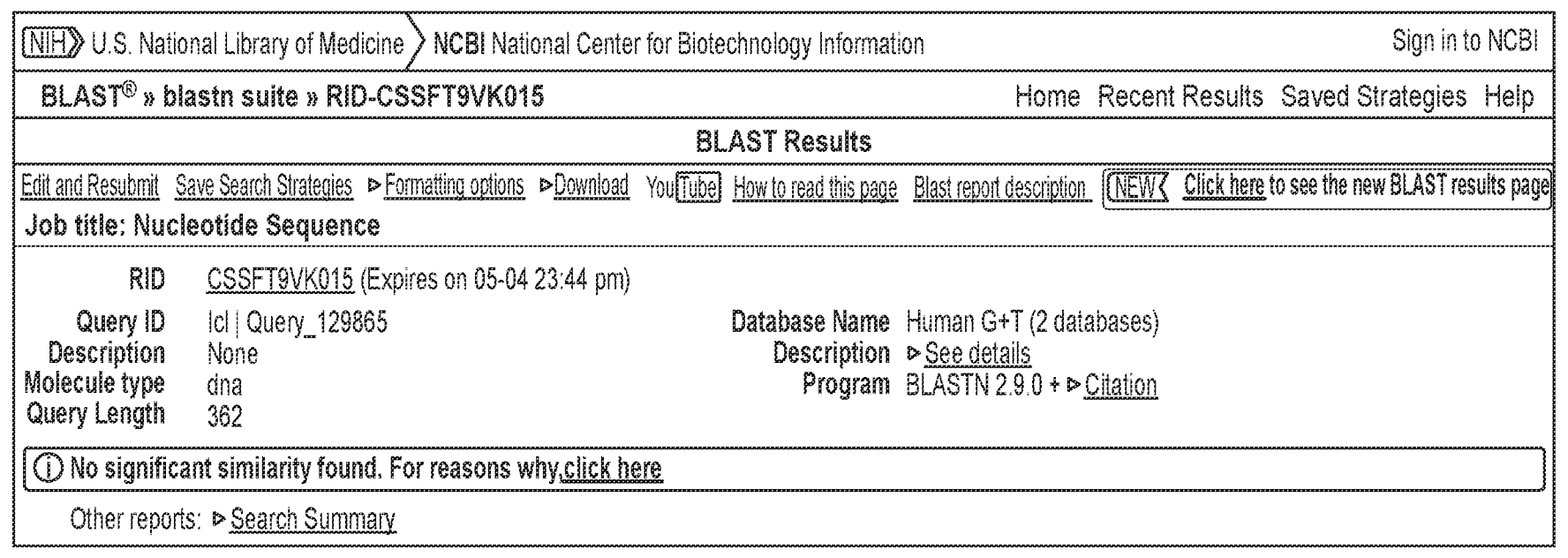

FIG. 1 is a screen shot of Blast results of the SdsDNA fragment against the Human genomic plus transcript (Human G+T) database. The NCBI Blast tool has many parameters available for conducting targeted DNA and RNA counterpart homology searches in deposited naturally occurring sequences. In FIG. 1, the entire 362 bp DNA fragment was run against the human genome and RNA transcript database. As the screen shot indicates, no perfect match was identified. This indicates the 362 bp fragment can be applied to human genomic and transcriptome quantitative studies.

FIG. 2 is a screen shot of Blast results of the SdsDNA fragment against the Nucleotide collection (nr/nt) database. The NCBI Blast tool has many parameters available for conducting targeted DNA and RNA counterpart homology searches in deposited naturally occurring sequences. In FIG. 2, the entire 362 bp DNA fragment was run against the entire known nucleotide collection database. As the screen shot indicates, no perfect match was identified. This indicates the 362 bp fragment can be applied to any known cellular genomic input.

FIG. 3 is a screen shot of Blast results of the SdsDNA fragment against the Reference RNA Sequences (refseq_rna) database. The NCBI Blast tool has many parameters available for conducting targeted DNA and RNA counterpart homology searches in deposited naturally occurring sequences. In FIG. 3, the entire 362 bp DNA fragment was run against the entire Reference RNA transcript database. As the screen shot indicates, no perfect match was identified. This indicates the 362 bp fragment can be applied to transcriptome quantitative studies.

FIG. 4 is a screen shot of Blast results of the SdsDNA fragment against the Human RefSeqGene sequences (RefSeqGene) database. The NCBI Blast tool has many parameters available for conducting targeted DNA and RNA counterpart homology searches in deposited naturally occurring sequences. In FIG. 4, the entire 362 bp DNA fragment was run against the entire RefSeqGene database. As the screen shot indicates, no perfect match was identified. This indicates the 362 bp fragment can be applied to human RefSeqGene quantitative studies.

FIG. 5 is a screen shot of Blast results of the SdsDNA fragment against the Patent database (pat) database. The NCBI Blast tool has many parameters available for conducting targeted DNA and RNA counterpart homology searches in deposited naturally occurring sequences. In FIG. 5, the entire 362 bp DNA fragment was run against the entire Genbank patent database. As the screen shot indicates, no perfect match was identified. This indicates the 362 bp fragment can be applied to transcriptome quantitative studies has no known prior art.

Figure 6:
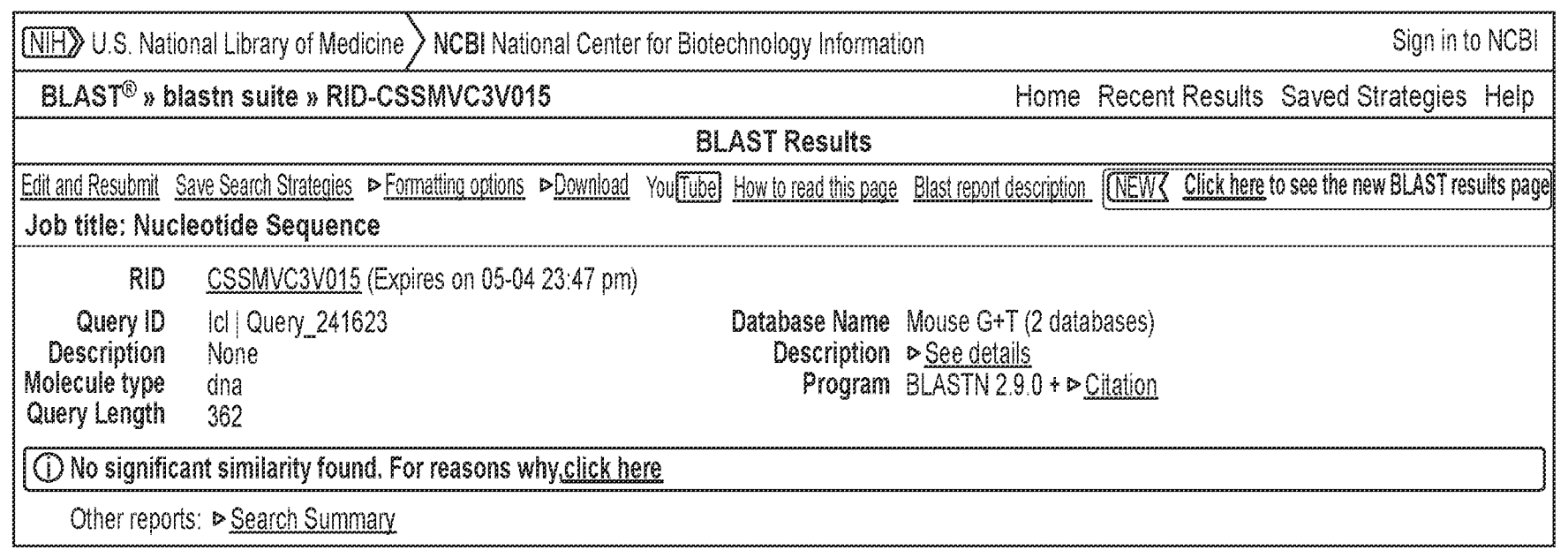

FIG. 6 is a screen shot of Blast results of the SdsDNA fragment against the Mouse genomic plus transcript (Mouse G+T) database. The NCBI Blast tool has many parameters available for conducting targeted DNA and RNA counterpart homology searches in deposited naturally occurring sequences. In FIG. 6, the entire 362 bp DNA fragment was run against the entire Mouse genomic plus transcriptomic database. As the screen shot indicates, no perfect match was identified. This indicates the 362 bp fragment can be applied to quantitative studies using mouse cells.

FIG. 7 is a screen shot of Blast results of the SdsDNA oligos against the Human genomic plus transcript (Mouse G+T) database. The NCBI Blast tool has many parameters available for conducting targeted DNA and RNA counterpart homology searches in deposited naturally occurring sequences. In FIG. 7, the SdsDNA primer oligos (SEQ ID NOS 2-3, respectively, in order of appearance) were ran against the entire Human genomic plus transcriptomic database. As the screen shot indicates, no perfect match was identified. This indicates the 362 bp fragment nested PCR amplification primers be applied to quantitative studies using human cells.

FIG. 8 is a screen shot of a Blast results of the SdsDNA oligos against the Human RefSeq mRNA database. The NCBI Blast tool has many parameters available for conducting targeted DNA and RNA counterpart homology searches in deposited naturally occurring sequences. In FIG. 8, the SdsDNA primer oligos (SEQ ID NOS 2-3, respectively, in order of appearance) were ran against the entire Human RefSeq mRNA database. As the screen shot indicates, no perfect match was identified. This indicates the 362 bp fragment nested PCR amplification primers be applied to quantitative studies using human cells, in particular for RNA and gene expression studies.

FIG. 9 is a screen shot of a Blast results of the SdsDNA oligos against the Mus musculus genome database. The NCBI Blast tool has many parameters available for conducting targeted DNA and RNA counterpart homology searches in deposited naturally occurring sequences. In FIG. 9, the SdsDNA primer oligos were ran against the entire mouse (Mus musculus) genomic database. As the screen shot indicates, no perfect match was identified. However, a partial match was identified and is unlikely to be amplified at stringent annealing temperatures of 55C-60C. Also, since this PCR product is predicted to be 2038 bp, this is highly unlikely to produce an efficient amplification product. This indicates the 362 bp fragment nested PCR amplification primers be applied to quantitative studies using mouse cells. FIG. 9 discloses SEQ ID NOS 2-3, 2, 4, 2, and 5, respectively, in order of appearance.

FIG. 10 is a screen shot of a Blast results of the SdsDNA oligos against the Mus musculus RefSeq mRNA database. The NCBI Blast tool has many parameters available for conducting targeted DNA and RNA counterpart homology searches in deposited naturally occurring sequences. In FIG. 10, the SdsDNA primer oligos (SEQ ID NOS 2-3, respectively, in order of appearance) were ran against the entire mouse (Mus musculus) RefSeq mRNA database. As the screen shot indicates, no perfect match was identified. This indicates the 362 bp fragment nested PCR amplification primers be applied to quantitative studies using mouse cells, in particular for RNA and gene expression studies.

DETAILED DESCRIPTION

Various aspects of the invention will now be described with reference to the following section which will be understood to be provided by way of illustration only and not to constitute a limitation on the scope of the invention.

"Complementarity" refers to the ability of a nucleic acid to form hydrogen bond(s) or hybridize with another nucleic acid sequence by either traditional Watson-Crick or other non-traditional types. As used herein "hybridization," refers to the binding, duplexing, or hybridizing of a molecule only to a particular nucleotide sequence under low, medium, or highly stringent conditions, including when that sequence is present in a complex mixture (e.g., total cellular) DNA or RNA. See e.g. Ausubel, et al., Current Protocols In Molecular Biology, John Wiley & Sons, New York, N.Y., 1993. If a nucleotide at a certain position of a polynucleotide is capable of forming a Watson-Crick pairing with a nucleotide at the same position in an anti-parallel DNA or RNA strand, then the polynucleotide and the DNA or RNA strand are complementary to each other at that position. The polynucleotide and the DNA or RNA molecule are "substantially complementary" to each other when a sufficient number of corresponding positions in each molecule are occupied by nucleotides that can hybridize or anneal with each other in order to affect the desired process. A complementary sequence is a sequence capable of annealing under stringent conditions to provide a 3'-terminal serving as the origin of synthesis of complementary chain.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. "Identity" and "similarity" can be readily calculated by known methods, including, but not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm may also be used to determine identity.

The terms "amplify", "amplifying", "amplification reaction" and their variants, refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated, on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR). In the present invention, the terms "synthesis" and "amplification" of nucleic acid are used. The synthesis of nucleic acid in the present invention means the elongation or extension of nucleic acid from an oligonucleotide serving as the origin of synthesis. If not only this synthesis but also the formation of other nucleic acid and the elongation or extension reaction of this formed nucleic acid occur continuously, a series of these reactions is comprehensively called amplification. The polynucleic acid produced by the amplification technology employed is generically referred to as an "amplicon" or "amplification product."

A number of nucleic acid polymerases can be used in the amplification reactions utilized in certain embodiments provided herein, including any enzyme that can catalyze the polymerization of nucleotides (including analogs thereof) into a nucleic acid strand. Such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also includes fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase or an aptamer-based polymerase that optionally can be reactivated.

The terms "target primer" or "target-specific primer" and variations thereof refer to primers that are complementary to a binding site sequence. Target primers are generally a single stranded or double-stranded polynucleotide, typically an oligonucleotide, that includes at least one sequence that is at least partially complementary to a target nucleic acid sequence.

"Forward primer binding site" and "reverse primer binding site" refers to the regions on the template DNA and/or the amplicon to which the forward and reverse primers bind. The primers act to delimit the region of the original template polynucleotide which is exponentially amplified during amplification. In some embodiments, additional primers may bind to the region 5' of the forward primer and/or reverse primers. Where such additional primers are used, the forward primer binding site and/or the reverse primer binding site may encompass the binding regions of these additional primers as well as the binding regions of the primers themselves. For example, in some embodiments, the method may use one or more additional primers which bind to a region that lies 5' of the forward and/or reverse primer binding region. Such a method was disclosed, for example, in WO0028082 which discloses the use of "displacement primers" or "outer primers".

A 'barcode' nucleic acid identification sequence can be incorporated into a nucleic acid primer or linked to a primer to enable independent sequencing and identification to be associated with one another via a barcode which relates information and identification that originated from molecules that existed within the same sample. There are numerous techniques that can be used to attach barcodes to the nucleic acids within a discrete entity. For example, the target nucleic acids may or may not be first amplified and fragmented into shorter pieces. The molecules can be combined with discrete entities, e.g., droplets, containing the barcodes. The barcodes can then be attached to the molecules using, for example, splicing by overlap extension. In this approach, the initial target molecules can have "adaptor" sequences added, which are molecules of a known sequence to which primers can be synthesized. When combined with the barcodes, primers can be used that are complementary to the adaptor sequences and the barcode sequences, such that the product amplicons of both target nucleic acids and barcodes can anneal to one another and, via an extension reaction such as DNA polymerization, be extended onto one another, generating a double-stranded product including the target nucleic acids attached to the barcode sequence. Alternatively, the primers that amplify that target can themselves be barcoded so that, upon annealing and extending onto the target, the amplicon produced has the barcode sequence incorporated into it. This can be applied with a number of amplification strategies, including specific amplification with PCR or non-specific amplification with, for example, MDA. An alternative enzymatic reaction that can be used to attach barcodes to nucleic acids is ligation, including blunt or sticky end ligation. In this approach, the DNA barcodes are incubated with the nucleic acid targets and ligase enzyme, resulting in the ligation of the barcode to the targets. The ends of the nucleic acids can be modified as needed for ligation by a number of techniques, including by using adaptors introduced with ligase or fragments to enable greater control over the number of barcodes added to the end of the molecule.

A barcode sequence can additionally be incorporated into microfluidic beads to decorate the bead with identical sequence tags. Such tagged beads can be inserted into microfluidic droplets and via droplet PCR amplification, tag each target amplicon with the unique bead barcode. Such barcodes can be used to identify specific droplets upon a population of amplicons originated from. This scheme can be utilized when combining a microfluidic droplet containing single individual cell with another microfluidic droplet containing a tagged bead. Upon collection and combination of many microfluidic droplets, amplicon sequencing results allow for assignment of each product to unique microfluidic droplets. In a typical implementation, we use barcodes on the Mission Bio Tapestri™ beads to tag and then later identify each droplet's amplicon content. The use of barcodes is described in U.S. patent application Ser. No. 15/940,850 filed Mar. 29, 2018 by Abate, A. et al., entitled 'Sequencing of Nucleic Acids via Barcoding in Discrete Entities', incorporated by reference herein.

In some embodiments, it may be advantageous to introduce barcodes into discrete entities, e.g., microdroplets, on the surface of a bead, such as a solid polymer bead or a hydrogel bead. These beads can be synthesized using a variety of techniques. For example, using a mix-split technique, beads with many copies of the same, random barcode sequence can be synthesized. This can be accomplished by, for example, creating a plurality of beads including sites on which DNA can be synthesized. The beads can be divided into four collections and each mixed with a buffer that will add a base to it, such as an A, T, G, or C. By dividing the population into four subpopulations, each subpopulation can have one of the bases added to its surface. This reaction can be accomplished in such a way that only a single base is added and no further bases are added. The beads from all four subpopulations can be combined and mixed together, and divided into four populations a second time. In this division step, the beads from the previous four populations may be mixed together randomly. They can then be added to the four different solutions, adding another, random base on the surface of each bead. This process can be repeated to generate sequences on the surface of the bead of a length approximately equal to the number of times that the population is split and mixed. If this was done 10 times, for example, the result would be a population of beads in which each bead has many copies of the same random 10-base sequence synthesized on its surface. The sequence on each bead would be determined by the particular sequence of reactors it ended up in through each mix-spit cycle.

A barcode may further comprise a 'unique identification sequence' (UMI). A UMI is a nucleic acid having a sequence which can be used to identify and/or distinguish one or more first molecules to which the UMI is conjugated from one or more second molecules. UMIs are typically short, e.g., about 5 to 20 bases in length, and may be conjugated to one or more target molecules of interest or amplification products thereof. UMIs may be single or double stranded. In some embodiments, both a nucleic acid barcode sequence and a UMI are incorporated into a nucleic acid target molecule or an amplification product thereof. Generally, a UMI is used to distinguish between molecules of a similar type within a population or group, whereas a nucleic acid barcode sequence is used to distinguish between populations or groups of molecules. In some embodiments, where both a UMI and a nucleic acid barcode sequence are utilized, the UMI is shorter in sequence length than the nucleic acid barcode sequence.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 97%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "nucleic acid," "polynucleotides," and "oligonucleotides" refers to biopolymers of nucleotides and, unless the context indicates otherwise, includes modified and unmodified nucleotides, and both DNA and RNA, and modified nucleic acid backbones. For example, in certain embodiments, the nucleic acid is a peptide nucleic acid (PNA) or a locked nucleic acid (LNA). Typically, the methods as described herein are performed using DNA as the nucleic acid template for amplification. However, nucleic acid whose nucleotide is replaced by an artificial derivative or modified nucleic acid from natural DNA or RNA is also included in the nucleic acid of the present invention insofar as it functions as a template for synthesis of complementary chain. The nucleic acid of the present invention is generally contained in a biological sample. The biological sample includes animal, plant or microbial tissues, cells, cultures and excretions, or extracts therefrom. In certain aspects, the biological sample includes intracellular parasitic genomic DNA or RNA such as virus or mycoplasma. The nucleic acid may be derived from nucleic acid contained in said biological sample. For example, genomic DNA, or cDNA synthesized from mRNA, or nucleic acid amplified on the basis of nucleic acid derived from the biological sample, are preferably used in the described methods. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U' denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

A template nucleic acid is a nucleic acid serving as a template for synthesizing a complementary chain in a nucleic acid amplification technique. A complementary chain having a nucleotide sequence complementary to the template has a meaning as a chain corresponding to the template, but the relationship between the two is merely relative. That is, according to the methods described herein a chain synthesized as the complementary chain can function again as a template. That is, the complementary chain can become a template. In certain embodiments, the template is derived from a biological sample, e.g., plant, animal, virus, micro-organism, bacteria, fungus, etc. In certain embodiments, the animal is a mammal, e.g., a human patient. A template nucleic acid typically comprises one or more target nucleic acid. A target nucleic acid in exemplary embodiments may comprise any single or double-stranded nucleic acid sequence that can be amplified or synthesized according to the disclosure, including any nucleic acid sequence suspected or expected to be present in a sample.

Primers and oligonucleotides used in embodiments herein comprise nucleotides. A nucleotide comprises any compound, including without limitation any naturally occurring nucleotide or analog thereof, which can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. For example, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

In some embodiments, the nucleotide comprises a label and referred to herein as a "labeled nucleotide"; the label of the labeled nucleotide is referred to herein as a "nucleotide label". In some embodiments, the label can be in the form of a fluorescent moiety (e.g. dye), luminescent moiety, or the like attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. a-thio-nucleotide 5'-triphosphates. For a review of nucleic acid chemistry, see: Shabarova, Z. and Bogdanov, A. Advanced Organic Chemistry of Nucleic Acids, VCH, New York, 1994.

Any nucleic acid amplification method may be utilized, such as a PCR-based assay, e.g., quantitative PCR (qPCR), or an isothermal amplification may be used to detect the presence of certain nucleic acids, e.g., genes, of interest, present in discrete entities or one or more components thereof, e.g., cells encapsulated therein. Such assays can be applied to discrete entities within a microfluidic device or a portion thereof or any other suitable location. The conditions of such amplification or PCR-based assays may include detecting nucleic acid amplification over time and may vary in one or more ways.

The number of amplification/PCR primers that may be added to a microdroplet may vary. The number of amplification or PCR primers that may be added to a microdroplet may range from about 1 to about 500 or more, e.g., about 2 to 100 primers, about 2 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more.

One or both primer of a primer set may also be attached or conjugated to an affinity reagent that may comprise anything that binds to a target molecule or moiety. Nonlimiting examples of affinity reagent include ligands, receptors, antibodies and binding fragments thereof, peptide, nucleic acid, and fusions of the preceding and other small molecule that specifically binds to a larger target molecule in order to identify, track, capture, or influence its activity. Affinity reagents may also be attached to solid supports, beads, discrete entities, or the like, and are still referenced as affinity reagents herein.

One or both primers of a primer set may comprise a barcode sequence described herein. In some embodiments, individual cells, for example, are isolated in discrete entities, e.g., droplets. These cells may be lysed and their nucleic acids barcoded. This process can be performed on a large number of single cells in discrete entities with unique barcode sequences enabling subsequent deconvolution of mixed sequence reads by barcode to obtain single cell information. This approach provides a way to group together nucleic acids originating from large numbers of single cells. Additionally, affinity reagents such as antibodies can be conjugated with nucleic acid labels, e.g., oligonucleotides including barcodes, which can be used to identify antibody type, e.g., the target specificity of an antibody. These reagents can then be used to bind to the proteins within or on cells, thereby associating the nucleic acids carried by the affinity reagents to the cells to which they are bound. These cells can then be processed through a barcoding workflow as described herein to attach barcodes to the nucleic acid labels on the affinity reagents. Techniques of library preparation, sequencing, and bioinformatics may then be used to group the sequences according to cell/discrete entity barcodes. Any suitable affinity reagent that can bind to or recognize a biological sample or portion or component thereof, such as a protein, a molecule, or complexes thereof, may be utilized in connection with these methods. The affinity reagents may be labeled with nucleic acid sequences that relates their identity, e.g., the target specificity of the antibodies, permitting their detection and quantitation using the barcoding and sequencing methods described herein. Exemplary affinity reagents can include, for example, antibodies, antibody fragments, Fabs, scFvs, peptides, drugs, etc. or combinations thereof. The affinity reagents, e.g., antibodies, can be expressed by one or more organisms or provided using a biological synthesis technique, such as phage, mRNA, or ribosome display. The affinity reagents may also be generated via chemical or biochemical means, such as by chemical linkage using N-Hydroxysuccinimide (NETS), click chemistry, or streptavidin-biotin interaction, for example. The oligo-affinity reagent conjugates can also be generated by attaching oligos to affinity reagents and hybridizing, ligating, and/or extending via polymerase, etc., additional oligos to the previously conjugated oligos. An advantage of affinity reagent labeling with nucleic acids is that it permits highly multiplexed analysis of biological samples. For example, large mixtures of antibodies or binding reagents recognizing a variety of targets in a sample can be mixed together, each labeled with its own nucleic acid sequence. This cocktail can then be reacted to the sample and subjected to a barcoding workflow as described herein to recover information about which reagents bound, their quantity, and how this varies among the different entities in the sample, such as among single cells. The above approach can be applied to a variety of molecular targets, including samples including one or more of cells, peptides, proteins, macromolecules, macromolecular complexes, etc. The sample can be subjected to conventional processing for analysis, such as fixation and permeabilization, aiding binding of the affinity reagents. To obtain highly accurate quantitation, the unique molecular identifier (UMI) techniques described herein can also be used so that affinity reagent molecules are counted accurately. This can be accomplished in a number of ways, including by synthesizing UMIs onto the labels attached to each affinity reagent before, during, or after conjugation, or by attaching the UMIs microfluidically when the reagents are used. Similar methods of generating the barcodes, for example, using combinatorial barcode techniques as applied to single cell sequencing and described herein, are applicable to the affinity reagent technique. These techniques enable the analysis of proteins and/or epitopes in a variety of biological samples to perform, for example, mapping of epitopes or post translational modifications in proteins and other entities or performing single cell proteomics. For example, using the methods described herein, it is possible to generate a library of labeled affinity reagents that detect an epitope in all proteins in the proteome of an organism, label those epitopes with the reagents, and apply the barcoding and sequencing techniques described herein to detect and accurately quantitate the labels associated with these epitopes.

Primers may contain primers for one or more nucleic acid of interest, e.g. one or more genes of interest. The number of primers for genes of interest that are added may be from about one to 500, e.g., about 1 to 10 primers, about 10 to 20 primers, about 20 to 30 primers, about 30 to 40 primers, about 40 to 50 primers, about 50 to 60 primers, about 60 to 70 primers, about 70 to 80 primers, about 80 to 90 primers, about 90 to 100 primers, about 100 to 150 primers, about 150 to 200 primers, about 200 to 250 primers, about 250 to 300 primers, about 300 to 350 primers, about 350 to 400 primers, about 400 to 450 primers, about 450 to 500 primers, or about 500 primers or more. Primers and/or reagents may be added to a discrete entity, e.g., a microdroplet, in one step, or in more than one step. For instance, the primers may be added in two or more steps, three or more steps, four or more steps, or five or more steps. Regardless of whether the primers are added in one step or in more than one step, they may be added after the addition of a lysing agent, prior to the addition of a lysing agent, or concomitantly with the addition of a lysing agent. When added before or after the addition of a lysing agent, the PCR primers may be added in a separate step from the addition of a lysing agent. In some embodiments, the discrete entity, e.g., a microdroplet, may be subjected to a dilution step and/or enzyme inactivation step prior to the addition of the PCR reagents. Exemplary embodiments of such methods are described in PCT Publication No. WO 2014/028378, the disclosure of which is incorporated by reference herein in its entirety and for all purposes.

A primer set for the amplification of a target nucleic acid typically includes a forward primer and a reverse primer that are complementary to a target nucleic acid or the complement thereof. In some embodiments, amplification can be performed using multiple target-specific primer pairs in a single amplification reaction, wherein each primer pair includes a forward target-specific primer and a reverse target-specific primer, where each includes at least one sequence that substantially complementary or substantially identical to a corresponding target sequence in the sample, and each primer pair having a different corresponding target sequence. Accordingly, certain methods herein are used to detect or identify multiple target sequences from a single cell sample.

In some implementations, solid supports, beads, and the like are coated with affinity reagents. Affinity reagents include, without limitation, antigens, antibodies or aptamers with specific binding affinity for a target molecule. The affinity reagents bind to one or more targets within the single cell entities. Affinity reagents are often detectably labeled (e.g., with a fluorophore). Affinity reagents are sometimes labeled with unique barcodes, oligonucleotide sequences, or UMI's.

In some implementations, a RT/PCR polymerase reaction and amplification reaction are performed, for example in the same reaction mixture, as an addition to the reaction mixture, or added to a portion of the reaction mixture.

In one particular implementation, a solid support contains a plurality of affinity reagents, each specific for a different target molecule but containing a common sequence to be used to identify the unique solid support. Affinity reagents that bind a specific target molecule are collectively labeled with the same oligonucleotide sequence such that affinity molecules with different binding affinities for different targets are labeled with different oligonucleotide sequences. In this way, target molecules within a single target entity are differentially labeled in these implements to determine which target entity they are from but contain a common sequence to identify them from the same solid support.

In another aspect, embodiments herein are directed at characterizing subtypes of cancerous and pre-cancerous cells at the single cell level. The methods provided herein can be used for not only characterization of these cells, but also as part of a treatment strategy based upon the subtype of cell. The methods provided herein are applicable to a wide variety of caners, including but not limited to the following: Acute Lymphoblastic Leukemia (ALL), Acute Myeloid Leukemia (AML), Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Astrocytomas, Atypical Teratoid/Rhabdoid Tumor, Childhood, Central Nervous System (Brain Cancer), Basal Cell Carcinoma, Bile Duct Cancer, Bladder Cancer. Childhood Bladder Cancer, Bone Cancer (includes Ewing Sarcoma and Osteosarcoma and Malignant Fibrous Histiocytoma), Brain Tumors, Breast Cancer, Childhood Breast Cancer, Bronchial Tumors, Burkitt Lymphoma (Non-Hodgkin Lymphoma, Carcinoid Tumor (Gastrointestinal), Childhood Carcinoid Tumors, Cardiac (Heart) Tumors, Central Nervous System tumors. Atypical Teratoid/Rhabdoid Tumor, Childhood (Brain Cancer), Embryonal Tumors, Childhood (Brain Cancer), Germ Cell Tumor (Childhood Brain Cancer), Primary CNS Lymphoma, Cervical Cancer, Childhood Cervical Cancer, Cholangiocarcinoma, Chordoma (Childhood), Chronic Lymphocytic Leukemia (CLL), Chronic Myelogenous Leukemia (CML), Chronic Myeloproliferative Neoplasms, Colorectal Cancer, Childhood Colorectal Cancer, Craniopharyngioma (Childhood Brain Cancer), Cutaneous T-Cell Lymphoma, Ductal Carcinoma In Situ (DCIS), Embryonal Tumors, (Childhood Brain CNS Cancers), Endometrial Cancer (Uterine Cancer), Ependymoma, Esophageal Cancer, Childhood Esophageal Cancer, Esthesioneuroblastoma (Head and Neck Cancer), Ewing Sarcoma (Bone Cancer), Extracranial Germ Cell Tumors, Extragonadal Germ Cell Tumors, Eye Cancer, Childhood Intraocular Melanoma, Intraocular Melanoma, Retinoblastoma, Fallopian Tube Cancer, Fibrous Histiocytoma of Bone (Malignant, and Osteosarcoma), Gallbladder Cancer, Gastric (Stomach) Cancer, Childhood Gastric (Stomach) Cancer, Gastrointestinal Carcinoid Tumor, Gastrointestinal Stromal Tumors (GIST) (Soft Tissue Sarcoma), Childhood Gastrointestinal Stromal Tumors, Germ Cell Tumors, Childhood Central Nervous System Germ Cell Tumors, Childhood Extracranial Germ Cell Tumors, Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis (Langerhans Cell Cancer), Hodgkin Lymphoma, Hypopharyngeal Cancer (Head and Neck Cancer), Intraocular Melanoma, Childhood Intraocular Melanoma, Islet Cell Tumors, (Pancreatic Neuroendocrine Tumors), Kaposi Sarcoma (Soft Tissue Sarcoma), Kidney (Renal Cell) Cancer, Langerhans Cell Histiocytosis, Laryngeal Cancer (Head and Neck Cancer), Leukemia, Lip and Oral Cavity Cancer (Head and Neck Cancer), Liver Cancer, Lung Cancer (Non-Small Cell and Small Cell), Childhood Lung Cancer, Lymphoma, Male Breast Cancer, Malignant Fibrous Histiocytoma of Bone and Osteosarcoma, Melanoma, Childhood Melanoma, Melanoma (Intraocular Eye), Childhood Intraocular Melanoma, Merkel Cell Carcinoma (Skin Cancer), Mesothelioma, Childhood Mesothelioma, Metastatic Cancer, Metastatic Squamous Neck Cancer with Occult Primary (Head and Neck Cancer), Midline Tract Carcinoma With NUT Gene Changes, Mouth Cancer (Head and Neck Cancer), Multiple Endocrine Neoplasia Syndromes—see Unusual Cancers of Childhood, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, Chronic (CML), Myeloid Leukemia, (Acute AML), Myeloproliferative Neoplasms, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer (Lip and Oral Cavity Cancer and Oropharyngeal Cancer), Osteosarcoma and Malignant Fibrous Histiocytoma of Bone, Ovarian Cancer, Childhood Ovarian Cancer, Pancreatic Cancer, Childhood Pancreatic Cancer, Pancreatic Neuroendocrine Tumors (Islet Cell Tumors), Papillomatosis, Paraganglioma, Childhood Paraganglioma, Paranasal Sinus and Nasal Cavity Cancer, Parathyroid Cancer, Penile Cancer, Pharyngeal Cancer, Pheochromocytoma, Childhood Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Prostate Cancer, Rectal Cancer, Recurrent Cancer, Renal Cell (Kidney) Cancer, Retinoblastoma, Rhabdomyosarcoma, Salivary Gland Cancer, Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sézary Syndrome (Lymphoma), Skin Cancer, Childhood Skin Cancer, Small Cell Lung Cancer, Small Intestine Cancer, Soft Tissue Sarcoma, Squamous Cell Carcinoma of the Skin, Squamous Neck Cancer with Occult Primary, Stomach (Gastric) Cancer, Childhood Stomach, T-Cell Lymphoma, Testicular Cancer, Childhood Testicular Cancer, Throat Cancer, Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter Kidney (Renal Cell Cancer), Ureter and Renal Pelvis (Transitional Cell Cancer Kidney Renal Cell Cancer), Urethral Cancer, Uterine Cancer (Endometrial), Uterine Sarcoma, Vaginal Cancer, Childhood Vaginal Cancer, Vascular Tumors (Soft Tissue Sarcoma), Vulvar Cancer, Wilms Tumor (and Other Childhood Kidney Tumors).

Embodiments of the invention may select target nucleic acid sequences for genes corresponding to oncogenesis, such as oncogenes, proto-oncogenes, and tumor suppressor genes. In some embodiments the analysis includes the characterization of mutations, copy number variations, and other genetic alterations associated with oncogenesis. Any known proto-oncogene, oncogene, tumor suppressor gene or gene sequence associated with oncogenesis may be a target nucleic acid that is studied and characterized alone or as part of a panel of target nucleic acid sequences. For examples, see Lodish H, Berk A, Zipursky SL, et al. Molecular Cell Biology. 4th edition. New York: W. H. Freeman; 2000. Section 24.2, Proto-Oncogenes and Tumor-Suppressor Genes, incorporated by reference herein.

Other aspects of the invention may be described in the follow embodiments:
1. A method for nucleic acid detection for single cell samples, the method comprising, independent of order presented, the following steps:
   i) selecting one or more target nucleic acid sequence of interest in an individual cell, wherein the target nucleic acid sequence is complementary to a nucleic acid in a cell;
   ii) providing a sample having a plurality of individual single cells and encapsulating one or more individual cell(s);
   iii) providing a sample normalization component to one or more encapsulated cell, wherein the normalization component comprises an exogenous nucleic acid having a known sequence;
   iv) providing nucleic acid primers for the target nucleic acid and the exogenous nucleic acid;
   v) providing a protease to each encapsulated cell and incubating the encapsulated cell with the protease to produce a cell lysate;
   vi) performing a nucleic acid amplification reaction to form an amplification product from the nucleic acid of a single cell, said amplification product comprising amplicons of one or more target nucleic acid sequence and an amplicon for the exogenous nucleic acid; and
   vii) comparing the amplification products from the target amplicons and the exogenous nucleic acid amplicons and determining the copy number or nucleotide sequence of the target nucleic acid in a single cell.
2. A method of embodiment 1 wherein in step iii) the sample normalization reagent comprises a synthetic nucleic acid having a known sequence.
3. A method of embodiment 1 wherein in step iii) the sample normalization reagent comprises an aliquot or portion of a cell extract comprising the exogenous nucleic acid.
4. A method according to embodiment 3, wherein the sample normalization reagent comprises a whole cell extract.
5. A method according to embodiment 3, wherein the cell extract comprising the exogenous nucleic acid is derived from a non-human cell line.
6. A method according to embodiment 1, wherein the synthetic nucleotide comprises a nucleotide sequence having at least 100 consecutive nucleotides of SEQ ID NO:1.
7. A method according to embodiment 1, wherein the synthetic nucleotide comprises SEQ ID NO:1.
8. A method according to embodiment 2, wherein the reaction mixture further comprises amplification primers complementary to the synthetic nucleic acid.
9. A method according to embodiment 3, wherein the amplification primers have nucleic acid sequences comprising SEQ ID NO:2 and SEQ ID NO:3.
10. A method according to embodiment 1, that includes providing a reverse transcriptase and comprises performing reverse transcription on the RNA to produce a reverse transcription product and amplifying the reverse transcription product, wherein performing reverse transcription and amplifying occur in a single step.
11. A method according to embodiment 1, further comprising performing a nucleic acid sequencing reaction of an amplification product.
12. A method according to embodiment 1, further comprising performing an analysis of the copy number variation of one or more selected target nucleic acid sequence.
13. A method according to embodiment 1, wherein an analysis of the copy number variation of one or more selected target nucleic acid sequence is performed and used to characterize one or more single cell.
14. A method according to embodiment 1, wherein an analysis of the copy number variation of one or more selected target nucleic acid sequence is performed and used to characterize one or more single cell to determine if the cell is mutated, pre-cancerous, or a cancer cell.
15. A method according to embodiment 1, wherein an analysis of a cancer cell pre-cancer cell subtype is performed.
16. A method according to embodiment 1, wherein an analysis includes a determination of structure variations, single nucleotide variations, or copy number variations or one or more target nucleic acid sequence.

17. A method according to embodiment 1 wherein and at least one primer of a nucleic acid amplification primer set comprises a barcode identification sequence and the method further comprises i) providing an affinity reagent that comprises a nucleic acid sequence complementary to the identification barcode sequence of one of more nucleic acid primer of a primer set, wherein said affinity reagent comprising said nucleic acid sequence complementary to the identification barcode sequence is capable of binding to a nucleic acid amplification primer set comprising a barcode identification sequence; and ii) contacting an affinity reagent to the amplification product comprising amplicons of one or more target nucleic acid sequence under conditions sufficient for binding of the affinity reagent to the target nucleic acid to form an affinity reagent bound target nucleic acid.

18. A method of embodiment 1 wherein in step iv) the amounts of the amplification products from the target amplicons and the exogenous nucleic acid amplicons are determined and compared.

19. A method according to embodiment 1, comprising performing reverse transcription to produce a reverse transcription product.

20. A method according to embodiment 1, comprising performing reverse transcription to produce a reverse transcription product before a nucleic acid amplification step.

21. A method according to embodiment 1, comprising performing reverse transcription on the RNA to produce a reverse transcription product and amplifying the reverse transcription product, wherein performing reverse transcription and amplifying occur in a single step.

22. A method according to embodiment 1, wherein the affinity reagent comprises a bead or solid support.

23. A method according to embodiment 1, wherein the synthetic nucleotide comprises a nucleotide sequence having at least 50 consecutive nucleotides of SEQ ID NO:1.

24. A method according to embodiment 1, wherein the synthetic nucleotide comprises a nucleotide sequence having at least 150 consecutive nucleotides of SEQ ID NO:1.

25. A method according to embodiment 1, wherein the synthetic nucleotide comprises a nucleotide sequence having at least 200 consecutive nucleotides of SEQ ID NO:1.

26. A method of identifying and characterizing clonal sub populations of cells, the method comprising the steps of:
i. selecting one or more target nucleic acid sequence of interest in an individual cell, wherein the target nucleic acid sequence is complementary to a nucleic acid in a cell;
ii. providing a sample having a plurality of individual single cells and encapsulating one or more individual cell(s);
iii. providing a sample normalization component to one or more encapsulated cell, wherein the normalization component comprises an exogenous nucleic acid having a known sequence;
iv. providing nucleic acid primers for the target nucleic acid and the exogenous nucleic acid;
v. providing a protease to each encapsulated cell and incubating the encapsulated cell with the protease in the drop to produce a cell lysate;
vi. performing a nucleic acid amplification reaction to form an amplification product from the nucleic acid of a single cell, said amplification product comprising amplicons of one or more target nucleic acid sequence and an amplicon for the exogenous nucleic acid; and
vii. comparing the amplification products from the target amplicons and the exogenous nucleic acid amplicons; and
viii. determining the copy number or sequence of the target nucleic acid in a single cell and using the copy number of one or more target nucleic acid to characterize a single cell.

27. A method of identifying and characterizing clonal sub populations of cells, the method comprising the steps of:
i. conjugating barcode sequences flanked by PCR priming sites onto antibodies, wherein a barcode sequence is specific to an antibody;
ii. performing a cell staining step using the barcode-conjugated antibodies;
iii. partitioning or separating individual cells or portion thereof and encapsulating one or more individual cell(s) or portion thereof in a reaction mixture comprising a protease and optionally a reverse transcriptase;
iv. providing a sample normalization component to one or more encapsulated cell, wherein the normalization component comprises an exogenous nucleic acid or polypeptide having a known sequence;
v. incubating the encapsulated cell with the protease;
vi. providing one or more nucleic acid amplification primer sets, wherein one or more primer of a primer set comprises a barcode identification sequence associated with an antibody;
vii. performing a nucleic acid amplification reaction to produce one or more amplicons;
viii. providing an affinity reagent that comprises a nucleic acid sequence complementary to the identification barcode sequence of one of more nucleic acid primer of a primer set, wherein said affinity reagent comprising said nucleic acid sequence complementary to the identification barcode sequence is capable of binding to a nucleic acid amplification primer set comprising a barcode identification sequence;
ix. contacting an affinity reagent to the amplification product comprising amplicons of one or more target nucleic acid sequence under conditions sufficient for binding of the affinity reagent to the target nucleic acid to form an affinity reagent bound target nucleic acid;
x. characterizing one or more protein by sequencing a barcode of an amplicon; and
xi. further characterizing the protein or nucleic acid that encodes the protein.

28. A method according to any of the preceding embodiments, further comprising performing a nucleic acid sequencing reaction of an amplification product.

29. A method according to any of the preceding embodiments, further comprising performing an analysis of the copy number variation of one or more selected target nucleic acid sequence.

30. A method according to any of the preceding embodiments, wherein an analysis of the copy number variation of one or more selected target nucleic acid sequence is performed and used to characterize one or more single cell.

31. A method according to any of the preceding embodiments, wherein an analysis of the copy number variation of one or more selected target nucleic acid sequence is performed and used to characterize one or more single cell to determine if the cell is mutated, pre-cancerous, or a cancer cell.
32. A method according to any of the preceding embodiments, wherein an analysis of a cancer cell pre-cancer cell subtype is performed.
33. A method according to any of the preceding embodiments, wherein an analysis includes a determination of structure variations, single nucleotide variations, or copy number variations or one or more target nucleic acid sequence.
34. An apparatus or system for performing a method described herein.
35. A composition or reaction mixture for performing a method described herein.
36. An antibody library generated by methods described herein.
37. A genomic library generated by methods described herein.
38. A transcriptome library generated according to a method described herein.
39. An antibody library, genomic, and transcriptome library generated according to a method described herein.
40. A kit for performing a method described herein.
41. A cell population selected by the methods described herein.
42. A method where signature mutations are identified at a single-cell level.
43. Amplification primer sets for the normalization of an amplification reaction, the primer sets selected from SEQ ID NO:2 and SEQ ID NO:3, and any other primer sets provided herein.

The following Examples are included for illustration and not limitation.

EXAMPLE I

Strategies to Normalize Quantitative Readouts in Single-cell Experiments

Microfluidic, droplet-based technology allows the quantitative interrogation of hundreds of analytes, in thousands of independent single cells in a single experiment, using PCR-based assays. Each drop acts as an independent microreactor.

Data normalization of multiplexed PCR-based assays using both endogenous controls and external reference samples, allows robust correction of differences in PCR efficiency, across independent samples and experiments. It is currently the gold standard 1, not only to understand sources of variability of laboratory developed tests (LDTs), but also to monitor assay performance metrics.

High-throughput single-cell experiments, by nature are quantitative, and intra- and/or inter-experimental normalization strategies are in high need. In our document, we describe two different approaches that will help to normalize quantitative, single-cell readouts.

Approach #1: Synthetic dsDNA Fragments

Tapestri® single-cell genomics workflow is based in two microfluidics-based steps: encapsulation, where the cells are individually compartmentalized into drops along with lysis buffer and protease/s. Next, the encapsulated drops are merged with a pool of gene-specific oligonucleotides, as well as PCR, barcoding reagents and hydrogel beads coated with cell barcoding constructs.

Synthetic double-stranded DNA (SdsDNA), can be spiked in, either during encapsulation and/or barcoding, at a controlled concentration of DNA molecules per drop. It can be used to calculate the number copies of certain genomic regions, chromosome or genome copies.

The relative quantification scheme can be illustrated in this microfluidic droplet example. If we assume each cell is encapsulated in the first droplet of a 100 pL volume, with 50 pL contributed by the lysis buffer. We can spike the exogenous DNA control at either 2, or 4, or 8, or 16, and so forth copies per 50 pL.

For example, assuming the exogenous DNA control has an identical barcoding and amplification efficiency as a targeted homozygous two-copy genomic DNA amplicon in an interrogated cell, if we select to spike the exogenous DNA control at 2 copies on average per droplet, then the amplicon read counts between the genomic DNA amplicon and the exogenous control SdsDNA should match within statistical confidence and statistical distribution. Similarly, if the exogenous DNA spike is at 16 copies on average per droplet, the ratio of genomic DNA amplicon read counts to spike DNA amplicon read counts should have a ratio of 8. If the cell is heterozygous, then each allele should have reads counts ½ of the spike in exogenous control. Likewise, if the cell is homozygous with a copy number amplification to four copies per cell, then the cell amplicon reads will be double that of a 2 copy per droplet spike of the SdsDNA.

For the first approach, we designed a SdsDNA fragment of 362 bp. The nucleotide sequence can be found in the Table 1. The sequence did not return positive matching against the Human genomic plus transcript (FIG. 1), Nucleotide collection (nr/nt; FIG. 2), Reference RNA Sequences (refseq_rna; FIG. 3), Human RefSeqGene sequences (RefSeq_Gene; FIG. 4), against the Patent database (pat; FIG. 5), nor the Mouse genomic plus transcript (Mouse G+T), using blastn algorithm.

This sequence was designed completely de novo and is not based on any known organism or gene source. The long synthetic construct can be manufactured in a laboratory setting by stitching together synthetic long oligonucleotide sequences (see Cold Spring Harbor Perspect Biol., 2017 January 3; 9(1):a023812.doi: 10.1101/cshperspect.a023812; Synthetic DNA Synthesis and Assembly: Putting the Synthetic in Synthetic Biology, Hughes, R. A., and Ellington, A. D., 2PMCID:PMC5204324, DOI: 10.1101/cshperspect.a023812).

Synthetic long DNA constructs are readily available from commercial suppliers (Origene, Rockview, Md. Blue Heron, Bothell, Wash.)

A pair of oligonucleotides was designed to amplify a 265 bp fragment of the SdsDNA. The sequence of the oligonucleotides can be found in Table 2 and also did not return positive matching against the Human genomic plus transcript (FIG. 7), nor the Human RefSeq mRNA (nr/nt; FIG. 8) databases.

Furthermore, multiple species of exogenous controls can be spiked at 2 copies, 4 copies, 8 copies 16 copies and 32 copies per first droplet to provide a linear calibration curve. Such curves can be used to normalize high levels of CNV in individual cells.

Approach #2: Cell Line/s

The second strategy of normalization described herein, would consist of mixing in each encapsulation or barcoding experiment, of an aliquot of cell line/s (either fixed, fresh or cryopreserved), along with the test sample/s of interest. The deconvolution of the cell barcoding system used in Tapestri, allows the identification at a single-cell level, of germline or somatic single-nucleotide variants (SNVs), di-nucleotide variants (DNVs), copy number variations (CNVs), patterns of gene and/or protein expression, associated to a particular cell type/s of the mixture.

Thus, after identifying the readouts differentially associated with the control cell line/s, the ratio of the sequencing depth (number of sequencing reads), across all the amplicons of a given panel, within the same sample type (cell line vs test sample), can be used as intra-sample normalization of PCR and/or reverse transcription efficiency. Since the same cell line/s will be used in each independent experiment, and Tapestri™ resolves the readouts at the single-cell level, it will also be used as an external reference sample. This has potential implications at different fronts. The inter-sample normalization of sequencing depth across all the amplicons, might also be helpful to identify changes in CNVs, gene or protein expression. In addition, can be a useful tool to monitor batch effects in manufacturing, but also for assay performance assessment through reproducibility test between different operators, laboratories, determination of dynamic ranges and limit of detection (LOD).

The assay performance assessment mentioned above is required for LDTs to be used in regulated environments such as CAP CLIA and ISO certified laboratories. The normalization strategies described herein can pave the way in incorporating single-cell proteo/genomics LTDs into the companion diagnostics space.

The advantage of using cell lines instead of purified DNA is that cell encased DNA more closely controls for cell lysis efficiency. Also, genomic DNA from intact cells is high molecular weight and should reflect initial PCR efficiencies indicative of experimental sample cells.

TABLE 1

Nucleotide sequence of the SdsDNA fragment (5'-3')

5' AGCTCTAGATCTCTAGGCTGGCTATAGGATCGAATCTCTAGCTTGCG
CGCGTATTTAGATATAGCTCTATTATCTTCCTAGAGAGAGAATTCTTCT
CTCTCTGCGCTGCTCGTATATATATTATACGTACGTAGTCGTAGCTAGC
TGATCGTAGCTCTCTAGCGCATGCAGGACTGAAGTATATTCTCTAGTCT
CTATCTTAGAGGATCGAGATGATGTGTCAGTCACTTTTATATAGAGGAG
CTCTTCTAGAGTCTCTTATTATAGGAGAGAGAGATTGCTCTTAGCTAGT
AGCTATTATATATGAGGAGAGCGCGCTCTTCTTAGATGCTAGCTGATCG
TACTCTTAGGAGCTTCTCTAG 3' (SEQ ID NO: 1)

Table 1 above displays the de novo designed synthetic double-stranded DNA (SdsDNA) spike-in amplicon sequence. This construct can be manufactured as depicted in FIG. 1B. This sequence does not have a known full-length homologous counterpart in nature, based upon NCBI BVlast homology searches.

Table 2 below shows the sequence and properties of the oligonucleotide pair used to amplify SdsDNA in Table 1.

| Name | Sequence 5'-3' | Length | GcContent | MeltTemp | MolecularWeight |
|---|---|---|---|---|---|
| FW | AAT TCT TCT CTC TCT GCG CTG (SEQ ID NO: 2) | 21 | 47.6 | 54.8 | 6314.1 |
| RV | TCC TAA GAG TAC GAT CAG CTA GC (SEQ ID NO: 3) | 23 | 47.8 | 55.3 | 7032.6 |

Table 2 displays desirable nested primer sequences to amplify a subpart of the 362 bp exogenous SdsDNA spike-in. These primers were selected to be compatible with microfluidic barcoding PCR cycling conditions.

Table 3 below shows the location and function of some tumor suppressor genes that are used for analysis, detection, examination or the like in embodiments of the invention, alone or in combination as a panel of genes or portions thereof.

| Gene | Familial Cancer Syndrome | Function | Chromosomal Location |
|---|---|---|---|
| TP53 | Li-Fraumeni syndrome | Cell cycle regulation, apoptosis | 17p13.1 |
| RB1 | Familial retinoblastoma | Cell cycle regulation | 13q14.1-q14.2 |
| p16(INK4a) | Familial melanoma | Cell cycle regulation | 9p21 |
| p14(ARF) | Familial melanoma | Mdm2 antagonist | 9p21 |
| CHK 1/2 | Li-Fraumeni syndrome | Protein kinase (G1 control) | 22q12.1 |
| KLF6 | Unknown | Transcriptional regulation | 10q21-q22 |
| NF1 | Neurofibromatosis type I | Catalysis of RAS inactivation | 17q11.2 |
| APC | Familial adenomatous polyposis | Inhibition of signal transduction | 5q21-q22 |

-continued

| Gene | Familial Cancer Syndrome | Function | Chromosomal Location |
| --- | --- | --- | --- |
| TSC1 | Tuberous sclerosis 1 | Interaction with tuberin | 9q34 |
| DCC | Deleted in colorectal carcinoma | Transmembrane receptor | 18q21.3 |
| BRCA1 | Familial breast cancer | Cell cycle, DNA repair | 17q21 |
| MSH2 | HNPCC1 | DNA mismatch repair | 2p22-p21 |
| MLH1 | HNPCC2 | DNA mismatch repair | 3p21.3 |
| PTEN | Cowden syndrome | PI-3 kinase signal transduction | 10q23.3 |
| LKB1 | Peutz-Jeghers syndrome | Phosphorylation and activation of AMPK | 19q13.3 |
| CDH1 | Familial diffuse gastric cancer | Cell-cell adhesion protein | 16q22.1 |
| TGF-R 1 | Unknown | Growth inhibition | 9q22.33-q31.1 |
| TGF-R II | Unknown | Growth inhibition | 3p24.1 |
| SMAD4 | Familial Juvenile polyposis syndrome | Regulation of TGF-β/BMP signaling | 18q21.1 |
| SMAD2 | Juvenile polyposis | TGF-β signal transduction | 18q21.1 |

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for nucleic acid detection for single cell samples, the method comprising, independent of order presented, the following steps:
   i) selecting one or more target nucleic acid sequences of interest in an individual cell, wherein a target nucleic acid sequence is complementary to a nucleic acid in a cell;
   ii) providing a sample having a plurality of individual single cells and encapsulating one or more individual cells;
   iii) providing a sample normalization component to one or more encapsulated cells, wherein the sample normalization component comprises an exogenous nucleic acid having a known sequence;
   iv) providing nucleic acid primers for a target nucleic acid and the exogenous nucleic acid, wherein at least one primer for a target nucleic acid sequence comprises a barcode identification sequence;
   v) providing a protease to each encapsulated cell and incubating the encapsulated cell with the protease to produce a cell lysate;

vi) performing a nucleic acid amplification reaction with the primers to form an amplification product from the nucleic acid of a single cell, said amplification product comprising amplicons of one or more target nucleic acid sequences and amplicons for the exogenous nucleic acid;

vii) providing an affinity reagent that comprises a nucleic acid sequence complementary to the barcode identification sequence, wherein said affinity reagent is capable of binding to a nucleic acid amplification primer set comprising the barcode identification sequence, and contacting the affinity reagent to the amplification product comprising amplicons of one or more target nucleic acid sequences under conditions sufficient for binding of the affinity reagent to an amplicon of a target nucleic acid comprising the barcode identification sequence to form an affinity reagent bound target nucleic acid amplicon; and viii) comparing amplicons of a target nucleic acid and amplicons of the exogenous nucleic acid and determining the copy number or nucleotide sequence of a target nucleic acid sequence in a single cell.

2. A method of claim 1 wherein the exogenous nucleic acid comprises a synthetic nucleic acid having a known sequence.

3. A method of claim 1 wherein in step iii) the sample normalization component comprises an aliquot of a cell extract comprising the exogenous nucleic acid.

4. A method according to claim 3, wherein the cell extract comprising the exogenous nucleic acid is derived from a non-human cell line.

5. A method according to claim 1, wherein the sample normalization component comprises a whole cell extract.

6. A method according to claim 1, wherein the exogenous nucleic acid comprises a nucleotide sequence having at least 100 consecutive nucleotides of SEQ ID NO:1.

7. A method according to claim 1, wherein the exogenous nucleic acid comprises SEQ ID NO:1.

8. A method according to claim 1, wherein the primers include a primer having a sequence comprising SEQ ID NO:2 and a primer having a sequence comprising SEQ ID NO:3.

9. A method according to claim 1, further comprising providing a reverse transcriptase and performing a reverse transcription to produce a reverse transcription product and amplifying the reverse transcription product.

10. A method according to claim 1, further comprising performing a nucleic acid sequencing reaction of an amplification product.

11. A method according to claim 1, further comprising performing an analysis of the copy number variation of one or more selected target nucleic acid sequences.

12. A method according to claim 1, wherein an analysis of the copy number variation of one or more selected target nucleic acid sequences is performed and used to characterize one or more single cells.

13. A method according to claim 1, wherein an analysis of the copy number variation of one or more selected target nucleic acid sequences is performed and used to characterize one or more single cells to determine if a cell is mutated, pre-cancerous, or a cancer cell.

14. A method according to claim 1, further comprising analyzing a cancer cell subtype or a pre-cancer cell subtype.

15. A method according to claim 1, further comprising determining structure variations, single nucleotide variations, or copy number variations of one or more target nucleic acid sequences.

16. A method of claim 1 wherein in step viii) the amount of amplicon of a target nucleic acid sequence and the amount of amplicon from the exogenous nucleic acid are determined and compared.

17. A method according to claim 1, further comprising performing reverse transcription to produce a reverse transcription product.

18. A method according to claim 1, further comprising performing reverse transcription to produce a reverse transcription product before a nucleic acid amplification step.

* * * * *

SEQUENCE LISTING

<160> NUMBER OF SEQ ID NOS: 5

<210> SEQ ID NO 1
<211> LENGTH: 362
<212> TYPE: DNA
<213> ORGANISM: Artificial Sequence
<220> FEATURE:

```
<223> OTHER INFORMATION: Description of Artificial Sequence: Synthetic
      polynucleotide

<400> SEQUENCE: 1
agctctagat ctctaggctg gctataggat cgaatctcta gcttgcgcgc gtatttagat      60
atagctctat tatcttccta gagagagaat tcttctctct ctgcgctgct cgtatatata     120
ttatacgtac gtagtcgtag ctagctgatc gtagctctct agcgcatgca ggactgaagt     180
atattctcta gtctctatct tagaggatcg agatgatgtg tcagtcactt ttatatagag     240
gagctcttct agagtctctt attataggag agagagattg ctcttagcta gtagctatta     300
tatatgagga gagcgcgctc ttcttagatg ctagctgatc gtactcttag gagcttctct     360
ag                                                                    362

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aattcttctc tctctgcgct g                                                21

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tcctaagagt acgatcagct agc                                              23

<210> SEQ ID NO 4
<211> LENGTH: 21
<212> TYPE: DNA
<213> ORGANISM: Mus musculus

<400> SEQUENCE: 4
tttctttctc tctctgtgct g                                                21

<210> SEQ ID NO 5
<211> LENGTH: 21
<212> TYPE: DNA
<213> ORGANISM: Mus musculus

<400> SEQUENCE: 5
gtctcgtctc tctcttaaga t                                                21
```